(12) United States Patent
Hormann et al.

(10) Patent No.: US 10,107,733 B2
(45) Date of Patent: Oct. 23, 2018

(54) SYSTEM AND METHOD OF SENSOR RECONDITIONING IN AN EXHAUST AFTERTREATMENT SYSTEM

(71) Applicant: Cummins Emission Solutions, Inc., Columbus, IN (US)

(72) Inventors: Matthew W. Hormann, Columbus, IN (US); Nathan Charles Schattke, Yorkville, IL (US)

(73) Assignee: Cummins Emission Solutions Inc., Columbus, IN (US)

( * ) Notice: Subject to any disclaimer, the term of this patent is extended or adjusted under 35 U.S.C. 154(b) by 0 days.

(21) Appl. No.: 15/522,509

(22) PCT Filed: Nov. 3, 2015

(86) PCT No.: PCT/US2015/058843
§ 371 (c)(1),
(2) Date: Apr. 27, 2017

(87) PCT Pub. No.: WO2016/073487
PCT Pub. Date: May 12, 2016

(65) Prior Publication Data
US 2017/0268979 A1    Sep. 21, 2017

Related U.S. Application Data

(60) Provisional application No. 62/075,060, filed on Nov. 4, 2014.

(51) Int. Cl.
*F01N 3/00* (2006.01)
*G01N 15/06* (2006.01)
(Continued)

(52) U.S. Cl.
CPC ....... *G01N 15/0656* (2013.01); *F01N 11/007* (2013.01); *G01N 15/0606* (2013.01);
(Continued)

(58) Field of Classification Search
CPC .. F01N 2560/05; F01N 2560/20; F01N 11/00; G01N 15/0606; G01N 15/0656; F02D 41/1494; G01R 33/50
See application file for complete search history.

(56) References Cited

U.S. PATENT DOCUMENTS

2008/0265870 A1    10/2008  Nair et al.
2012/0260636 A1*   10/2012  Hashida .................. F01N 11/00
                                                                60/276

(Continued)

FOREIGN PATENT DOCUMENTS

CN        1554860       12/2004
DE   10 2012 214 974     2/2014

OTHER PUBLICATIONS

International Search Report and Written Opinion issued for PCT/US2015/058843, dated Jan. 14, 2016, 9 pages.

*Primary Examiner* — Mark Laurenzi
*Assistant Examiner* — Anthony Ayala Delgado
(74) *Attorney, Agent, or Firm* — Foley & Lardner LLP

(57) ABSTRACT

The present disclosure relates to a system, apparatus, and method for reconditioning a particulate matter sensor in an exhaust aftertreatment system that will resist poisoning. The system and method includes receiving particulate matter data indicating a state of the particulate matter sensor; determining that the particulate matter sensor is in a full state based on the particulate matter data; activating a heating element of the particulate matter sensor to a multiple of intermittent temperatures that clean the sensor pre-patory to the next measurement. By this manner, many reactive chemicals are removed before they can react with and poison the sensor materials.

18 Claims, 32 Drawing Sheets

(51) Int. Cl.
   *F01N 11/00* (2006.01)
   *G01N 15/00* (2006.01)
(52) U.S. Cl.
   CPC ...... *F01N 2560/05* (2013.01); *F01N 2560/20* (2013.01); *G01N 2015/0046* (2013.01)

(56) References Cited

U.S. PATENT DOCUMENTS

2013/0000678 A1    1/2013  Hocken et al.
2014/0216014 A1    8/2014  Hashida et al.
2017/0307501 A1*  10/2017  Shimokawa ....... G01N 15/0806

* cited by examiner

| ID | CHEMICALS | DETAILS | PN FISHER | AMT FISHER | COST FISHER | CAS | DOLPHIN NUMBER | DOLPHIN Y/N | SOLUBILITY DANGER |
|---|---|---|---|---|---|---|---|---|---|
| Chs | HIGH SURFACE AREA CARBON | PRINTEX U FROM EVONIK/DEGUSSA | | | | | | YES | 0 |
| N | NITRIC ACID | | | | | | | YES | 1 |
| S | SULFURIC ACID | | | | | | | YES | 1 |
| NH3 | AMMONIA | | S25164A | 1000ml | 7 | | | YES | 1 |
| Fe | IRON | Aldr 12310 | AA80737A1 | 1000g | 138 | 7439-89-6 | 42311 | NO | 0 |
| Rs | RUST SMALL | Aldr 544884 | | | | 1309-37-1 | NO, aa-0151 | YES | 1 |
| Rl | RUST LARGE | Aldr 310050 | AC19326-0100 | 10g | 120 | | | NO | 0 |
| Fe3S | IRON(III) SULFATE | Aldr 307718 | 50-901-14650 | 250g | 47 | 15244-10-7 | NO, REQ AA-0157 | NO | 0.5 |
| Fe2S | IRON(II) SULFATE | Aldr 215422 | AC423731000 | 100g | 24 | 7782-63-0 | 34713 | YES | 0.5 |
| FeN | IRON(III) NITRATE | Aldr 216828 | 1110-100 | 100g | 75 | 7782-61-8 | 35132 | YES | 1 |
| FeCl | IRON CHLORIDE | Aldr 236489 | AC217091000 | 100g | 33 | 10025-77-1 | 34710, AA-0158 | NO | 1 |
| CaN | CALCIUM NITRATE | Aldr C1396 | AC42353-0250 | 25g | 15 | 13477-34-4 | NO, AA-0159 | NO | 1 |
| CuN | COPPER NITRATE | Aldr 61194 | AC20766-0050 | 5g | 15 | 10031-43-3 | NO, AA-0160 | NO | 1 |
| CuCl | COPPER CHLORIDE | Aldr 212946 | AC19964-0250 | 25g | 34 | 7758-89-6 | 27184 | YES | 1 |
| KNO3 | KNO3 SALT PETER | Aldr P8394 | AC42415-1000 | 100g | 39 | 7757-79-1 | 904141 | YES | 1 |
| NaCl | SODIUM CHLORIDE (SALT) | | | | | | | | |
| MgS | MgSO4 | Aldr 208094 | AC44689-2500 | 250g | 68 | 7487-88-9 | 901482 | YES | 1 |
| Zn | ZnSO4 | Aldr Z4750 | AC20598-2500 | 250g | 31 | 7446-20-0 | 34352 | YES | 1 |
| Mn | MnSO4 | Aldr 31425 | AC42391-0050 | 5g | 28 | 10034-96-5 | NO, AA-0162 | NO | 1 |
| P | PHOSPHORIC ACID | | S25470 | 100ml | 9 | 7664-38-2 | | YES | 1 |
| U | UREA | | | | | | | YES | 1 |
| KCl | KCl | Aldr P3911 | AC42409B250 | 25g | 28 | 7447-40-7 | 68176 | YES | 1 |

| BAKING ENVIRONMENT | PARTS | |
|---|---|---|
| O2 | 10 | |
| H2O | 4 | |
| CO2 | 3 | |
| CO | 0.01 | |
| PROPANE OR OTHER HYDROCARBON | 0.1 | |
| NO2 | 0.04 | |
| NO | 0.01 | |
| N2 | 82.84 | BALANCE |
| FLOW RATE | 10 | L/min |

505

| | LENGTH mm | WIDTH mm | mm^2 | mm^3 |
|---|---|---|---|---|
| TEST SURFACE AREA | 3.3 | 2.3 | 7.59 | 0.759 |
| TARGET THICKNESS | 0.1 | | cm^3 | 0.000759 |

503

| BAKING PROTOCOL | | NOTE: RAMP RATE DICTATED BY TIME DIFFERENCE | |
|---|---|---|---|
| | START (MIN) | END (MIN) | TEMP C | |
| A | 0 | 5 | 100 | START GAS AFTER TEMP REACHED |
| | 15 | 30 | 275 | |
| | 50 | | 100 | |
| B | 0 | 5 | 100 | START GAS AFTER TEMP REACHED |
| | 20 | 35 | 450 | |
| | 90 | | 100 | |
| C | 0 | 5 | 100 | START GAS AFTER TEMP REACHED |
| | 40 | 55 | 800 | |
| | 120 | | 100 | |
| REF | 2012 H2SO4 ON SOOT | | SEE GRAPH | |

502

| EQUIPMENT | DETAILS |
|---|---|
| RESISTANCE METER | 0.01 ohms TO meg ohms |
| IMPEDANCE METER | 1 TO meg Hz |
| GAS MIXING DEVICE | SEE BAKING ENVIRONMENT |
| POWER SUPPLY | 5 TO 20 V, 1 mA to 500 mA |
| GENERAL CHEMISTRY | MIX, DILUTE, STORE-USE MICROCHEMISTRY KIT |
| DISPENSING | PASTURE PIPETTE |

| EXP ID | Cbs | Ni | S | NH3 | Fe | Rs | Ri | Fe3S | Fe2S | FeN | FeCl | CaN | CuN | CuCl | KNO3 | NaCl | MgS | Zn | Mn | P | U | KCl | CHECK | BAKING PROTOCOL |
|---|---|---|---|---|---|---|---|---|---|---|---|---|---|---|---|---|---|---|---|---|---|---|---|---|
| FN1 | | | | | | | | | | 100 | | | | | | | | | | | | | 100 | A,TEST,REDOSE,B,TEST,REDOSE,C,TEST |
| FN2 | | 20 | | | | | | | | 80 | | | | | | | | | | | | | 100 | A,TEST,REDOSE,B,TEST,REDOSE,C,TEST |
| FN5 | | 80 | | | | | | | | 20 | | | | | | | | | | | | | 100 | A,TEST,REDOSE,B,TEST,REDOSE,C,TEST |
| FN6 | 10 | 10 | | | | | | | | 80 | | | | | | | | | | | | | 100 | A,TEST,REDOSE,B,TEST,REDOSE,C,TEST |
| FN7 | 30 | 10 | | | | | | | | 60 | | | | | | | | | | | | | 100 | A,TEST,REDOSE,B,TEST,REDOSE,C,TEST |
| FN8 | 50 | 10 | | | | | | | | 40 | | | | | | | | | | | | | 100 | A,TEST,REDOSE,B,TEST,REDOSE,C,TEST |
| FN10 | 20 | 10 | | | | | | | | 60 | | | | | | | | | | | | | 100 | A,TEST,REDOSE,B,TEST,REDOSE,C,TEST |
| ECS 869b | 90 | | | | 10 | | | | | | | | | | | | | | | | | | 100 | A,TEST,REDOSE,B,TEST,REDOSE,C,TEST |
| ECS 869d | 90 | 5 | | | 5 | 5 | | | | | | | | | | | | | | | | | 100 | A,TEST,REDOSE,B,TEST,REDOSE,C,TEST |
| IHSABa | 90 | 5 | | | | 5 | 5 | | | | | | | | | | | | | | | | 100 | A,TEST,REDOSE,B,TEST,REDOSE,C,TEST |
| IHSABb | 90 | | | 5 | | 5 | 5 | | | | | | | | | | | | | | | | 100 | A,TEST,REDOSE,B,TEST,REDOSE,C,TEST |
| IHSABc | 90 | | | 5 | | 5 | 5 | | | | | | | | | | | | | | | | 100 | A,TEST,REDOSE,B,TEST,REDOSE,C,TEST |
| IHSABd | 90 | | | | | 5 | 5 | | | | | | | | 5 | | | | | | | | 100 | A,TEST,REDOSE,B,TEST,REDOSE,C,TEST |
| IHSABe | 90 | 5 | | | | 10 | | | | | | | | | | | | | | | | | 100 | A,TEST,REDOSE,B,TEST,REDOSE,C,TEST |
| IHSABf | 90 | | | | | 10 | | | | | | 10 | | | | | 10 | | | | | | 100 | A,TEST,REDOSE,B,TEST,REDOSE,C,TEST |
| IHSABg | 80 | | 5 | 5 | 5 | | | | | | | | | | | | | | | | | 20 | 100 | A,TEST,REDOSE,B,TEST,REDOSE,C,TEST |
| ECS 585a | 70 | | 10 | | | | | 50 | | | | | | | | | | | | | | | 100 | A,TEST,REDOSE,B,TEST,REDOSE,C,TEST |
| ECS 585e | 70 | | 10 | | | | | | 50 | | | | | | | | | | | | | | 100 | A,TEST,REDOSE,B,TEST,REDOSE,C,TEST |
| FORMb | 50 | | | | | 50 | | | | 50 | | | | | | | | | | | | | 100 | A,TEST,REDOSE,B,TEST,REDOSE,C,TEST |
| FORMc | 50 | | | | 50 | | | | | | 50 | | | | | | | | | | | | 100 | A,TEST,REDOSE,B,TEST,REDOSE,C,TEST |
| FORMe | 50 | | | | 50 | | | | | | | | | | | | | | | | | | 100 | A,TEST,REDOSE,B,TEST,REDOSE,C,TEST |
| FORMf | 50 | | | | | | | | | | | | | | | | | | | | | | 100 | A,TEST,REDOSE,B,TEST,REDOSE,C,TEST |
| FORMg | 50 | | | | | | | | | | | | | | | | | | | | | | 100 | A,TEST,REDOSE,B,TEST,REDOSE,C,TEST |
| FORMh | 50 | | | | | | | | | | | | | | | | | | | | | | 100 | A,TEST,REDOSE,B,TEST,REDOSE,C,TEST |

FIG. 6B

| ELEMENT | RANK A | EXP ID | Chs | N | S | NH3 | Fe | Rs | R1 | Fe3S | Fe2S | FeN | FeCl | CoN | CuN | CuCl | KNO3 | NaCl | MgS | Zn | Mn | P | U | KCl |
|---|---|---|---|---|---|---|---|---|---|---|---|---|---|---|---|---|---|---|---|---|---|---|---|---|
| FN1 | 3 | FN1 | 0 | 0 | 0 | 0 | 0 | 0 | 0 | 0 | 0 | 0.05 | 0 | 0 | 0 | 0 | 0 | 0 | 0 | 0 | 0 | 0 | 0 | 0 |
| FN2 | 16 | FN2 | 0 | 0.01 | 0 | 0 | 0 | 0 | 0 | 0 | 0 | 0.04 | 0 | 0 | 0 | 0 | 0 | 0 | 0 | 0 | 0 | 0 | 0 | 0 |
| FN5 | 1 | FN5 | 0 | 0.04 | 0 | 0 | 0 | 0 | 0 | 0 | 0 | 0.01 | 0 | 0 | 0 | 0 | 0 | 0 | 0 | 0 | 0 | 0 | 0 | 0 |
| FN6 | 23 | FN6 | 0.005 | 0.005 | 0 | 0 | 0 | 0 | 0 | 0 | 0 | 0.04 | 0 | 0 | 0 | 0 | 0 | 0 | 0 | 0 | 0 | 0 | 0 | 0 |
| FN7 | 5 | FN7 | 0.015 | 0.005 | 0 | 0 | 0 | 0 | 0 | 0 | 0 | 0.03 | 0 | 0 | 0 | 0 | 0 | 0 | 0 | 0 | 0 | 0 | 0 | 0 |
| FN8 | 4 | FN8 | 0.025 | 0.005 | 0 | 0 | 0 | 0 | 0 | 0 | 0 | 0.02 | 0 | 0 | 0 | 0 | 0 | 0 | 0 | 0 | 0 | 0 | 0 | 0 |
| FN10 | 37 | FN10 | 0.01 | 0 | 0 | 0 | 0 | 0 | 0 | 0 | 0 | 0.03 | 0 | 0 | 0 | 0 | 0 | 0 | 0 | 0 | 0 | 0 | 0.01 | 0 |
| ECS 869b | 22 | ECS 869b | 0.045 | 0 | 0 | 0 | 0.005 | 0 | 0 | 0 | 0 | 0 | 0 | 0 | 0 | 0 | 0 | 0 | 0 | 0 | 0 | 0 | 0 | 0 |
| ECS 869d | 10 | ECS 869d | 0.045 | 0.0025 | 0 | 0 | 0.0025 | 0 | 0 | 0 | 0 | 0 | 0 | 0 | 0 | 0 | 0 | 0 | 0 | 0 | 0 | 0 | 0 | 0 |
| IHSABa | | IHSABa | 0.045 | 0.0025 | 0 | 0 | 0 | 0.0025 | 0 | 0 | 0 | 0 | 0 | 0 | 0 | 0 | 0 | 0 | 0 | 0 | 0 | 0 | 0 | 0 |
| IHSABb | 2 | IHSABb | 0.045 | 0.0025 | 0 | 0.0025 | 0 | 0.0025 | 0.0025 | 0 | 0 | 0 | 0 | 0 | 0 | 0 | 0 | 0 | 0 | 0 | 0 | 0 | 0 | 0 |
| IHSABc | | IHSABc | 0.045 | 0 | 0 | 0.0025 | 0 | 0.0025 | 0 | 0 | 0 | 0 | 0 | 0 | 0 | 0 | 0 | 0 | 0 | 0 | 0 | 0 | 0 | 0 |
| IHSABd | 35 | IHSABd | 0.045 | 0 | 0 | 0 | 0 | 0.0025 | 0.0025 | 0 | 0 | 0 | 0 | 0 | 0 | 0 | 0 | 0 | 0 | 0 | 0 | 0 | 0 | 0 |
| IHSABe | | IHSABe | 0.045 | 0 | 0.0025 | 0 | 0 | 0.0025 | 0 | 0 | 0 | 0 | 0 | 0 | 0 | 0 | 0 | 0 | 0 | 0 | 0 | 0 | 0 | 0 |
| IHSABf | 9 | IHSABf | 0.045 | 0.0025 | 0.0025 | 0 | 0.0025 | 0 | 0 | 0 | 0 | 0 | 0 | 0 | 0 | 0 | 0 | 0 | 0 | 0 | 0 | 0 | 0 | 0 |
| IHSABg | 38 | IHSABg | 0.04 | 0 | 0 | 0 | 0 | 0.005 | 0 | 0 | 0 | 0 | 0 | 0.005 | 0 | 0 | 0 | 0 | 0 | 0 | 0 | 0 | 0 | 0 |
| ECS 585a | 32 | ECS 585a | 0.035 | 0.005 | 0 | 0 | 0 | 0.005 | 0 | 0 | 0 | 0 | 0 | 0 | 0 | 0.003 | 0 | 0 | 0 | 0 | 0 | 0 | 0 | 0 |
| ECS 585e | 8 | ECS 585e | 0.035 | 0 | 0 | 0 | 0 | 0.005 | 0 | 0 | 0 | 0 | 0 | 0 | 0 | 0 | 0 | 0.005 | 0 | 0 | 0 | 0 | 0 | 0 |
| FORMb | 14 | FORMb | 0.025 | 0 | 0 | 0 | 0 | 0 | 0 | 0 | 0 | 0 | 0 | 0 | 0 | 0 | 0 | 0 | 0 | 0 | 0 | 0 | 0 | 0 |
| FORMc | 12 | FORMc | 0.025 | 0 | 0 | 0 | 0 | 0 | 0 | 0 | 0.025 | 0 | 0 | 0 | 0 | 0 | 0 | 0 | 0 | 0 | 0 | 0 | 0 | 0 |
| FORMe | 13 | FORMe | 0.025 | 0 | 0 | 0 | 0 | 0 | 0 | 0.025 | 0 | 0 | 0 | 0 | 0 | 0 | 0 | 0 | 0 | 0 | 0 | 0 | 0 | 0 |
| FORMf | 19 | FORMf | 0.025 | 0 | 0 | 0 | 0 | 0 | 0 | 0 | 0 | 0.025 | 0.025 | 0 | 0 | 0 | 0 | 0 | 0 | 0 | 0 | 0 | 0 | 0 |
| FORMg | 28 | FORMg | 0.025 | 0 | 0 | 0 | 0.025 | 0.025 | 0 | 0 | 0 | 0 | 0 | 0 | 0 | 0 | 0 | 0 | 0 | 0 | 0 | 0 | 0 | 0 |
| FORMh | | FORMh | 0.025 | 0 | 0 | 0 | 0 | 0.025 | 0 | 0 | 0 | 0 | 0.025 | 0 | 0 | 0 | 0 | 0 | 0 | 0 | 0 | 0 | 0 | 0 |

| EXP ID | Chs | M | S | NH3 | Fe | Rs | RI | Fe3S | Fe2S | FeM | FeCl | CaM | CuM | CuCl | KNO3 | NaCl | MgS | Zn | Mn | P | U | KCl |
|---|---|---|---|---|---|---|---|---|---|---|---|---|---|---|---|---|---|---|---|---|---|---|
| FM1 | 0 | 0 | 0 | 0 | 0 | 0 | 0 | 0 | 0 | 0.0488 | 0 | 0 | 0 | 0 | 0 | 0 | 0 | 0 | 0 | 0 | 0 | 0 |
| FM2 | 0 | 0.01 | 0 | 0 | 0 | 0 | 0 | 0 | 0 | 0.039 | 0 | 0 | 0 | 0 | 0 | 0 | 0 | 0 | 0 | 0 | 0 | 0 |
| FM5 | 0 | 0.04 | 0 | 0 | 0 | 0 | 0 | 0 | 0 | 0.0124 | 0 | 0 | 0 | 0 | 0 | 0 | 0 | 0 | 0 | 0 | 0 | 0 |
| FM6 | 0.0059 | 0.005 | 0 | 0 | 0 | 0 | 0 | 0 | 0 | 0.039 | 0 | 0 | 0 | 0 | 0 | 0 | 0 | 0 | 0 | 0 | 0 | 0 |
| FM7 | 0.0146 | 0.005 | 0 | 0 | 0 | 0 | 0 | 0 | 0 | 0.0316 | 0 | 0 | 0 | 0 | 0 | 0 | 0 | 0 | 0 | 0 | 0 | 0 |
| FM8 | 0.0216 | 0.005 | 0 | 0 | 0 | 0 | 0 | 0 | 0 | 0.0244 | 0 | 0 | 0 | 0 | 0 | 0 | 0 | 0 | 0 | 0 | 0 | 0 |
| FM10 | 0.0094 | 0 | 0 | 0 | 0 | 0 | 0 | 0 | 0 | 0.0334 | 0 | 0 | 0 | 0 | 0 | 0 | 0 | 0 | 0 | 0 | 0 | 0 |
| ECS 869B | 0.0445 | 0 | 0 | 0 | 0.06 | 0 | 0 | 0 | 0 | | 0 | 0 | 0 | 0 | 0 | 0 | 0 | 0 | 0 | 0 | 0 | 0 |
| ECS 869D | 0.0357 | 0.0025 | 0 | 0 | 0.0044 | 0 | 0 | 0 | 0 | | 0 | 0 | 0 | 0 | 0 | 0 | 0 | 0 | 0 | 0 | 0 | 0 |
| IHSAB6 | 0.0455 | 0.0025 | 0 | 0 | 0 | 0 | 0.0023 | 0 | 0 | 0 | 0 | 0 | 0 | 0 | 0 | 0 | 0 | 0 | 0 | 0 | 0 | 0 |
| IHSAB4 | 0.0479 | 0 | 0 | 0.0025 | 0 | 0 | 0.0031 | 0 | 0 | 0 | 0 | 0 | 0 | 0 | 0 | 0 | 0 | 0 | 0 | 0 | 0 | 0 |
| IHSAB7 | 0.0416 | 0 | 0.0025 | 0 | 0 | 0 | 0.0027 | 0 | 0 | 0 | 0 | 0 | 0 | 0 | 0 | 0 | 0 | 0 | 0 | 0 | 0 | 0 |
| IHSAB9 | 0.0395 | 0.0025 | 0 | 0 | 0.0034 | 0 | 0.0036 | 0 | 0 | 0 | 0 | 0 | 0 | 0 | 0 | 0 | 0 | 0 | 0 | 0 | 0 | 0 |
| ECS 585A | 0.032 | 0 | 0.005 | 0 | 0 | 0 | 0.0063 | 0 | 0 | 0 | 0 | 0 | 0 | 0 | 0 | 0 | 0 | 0 | 0 | 0 | 0 | 0 |
| ECS 585E | 0.0313 | 0.005 | 0 | 0 | 0 | 0 | 0.0055 | 0 | 0 | 0 | 0 | 0 | 0 | 0 | 0 | 0 | 0 | 0 | 0 | 0 | 0 | 0 |
| FORMB | 0.0292 | 0 | 0 | 0 | 0 | 0 | 0 | 0.0208 | 0 | 0 | 0 | 0 | 0 | 0 | 0 | 0 | 0 | 0 | 0 | 0 | 0 | 0 |
| FORMC | 0.0243 | 0 | 0 | 0 | 0 | 0 | 0 | 0 | 0.0249 | 0 | 0 | 0 | 0 | 0 | 0 | 0 | 0 | 0 | 0 | 0 | 0 | 0 |
| FORME | 0.0233 | 0 | 0 | 0 | 0 | 0 | 0 | 0 | 0 | 0.0251 | 0 | 0.0067 | 0 | 0 | 0 | 0 | 0 | 0 | 0 | 0 | 0 | 0 |
| FORMF | 0.0480 | 0 | 0 | 0 | 0 | 0 | 0 | 0 | 0 | 0 | 0.0279 | 0 | 0 | 0 | 0 | 0 | 0.0061 | 0 | 0 | 0 | 0.0121 | 0 |
| FORMG | 0.0298 | 0 | 0 | 0 | 0.023 | 0 | 0 | 0 | 0 | 0 | 0 | 0 | 0 | 0 | 0.0018 | 0 | 0 | 0 | 0 | 0 | 0 | 0 |

FIG. 7A

| | | | | | | | | | | | | | | | | | | | |
|---|---|---|---|---|---|---|---|---|---|---|---|---|---|---|---|---|---|---|---|
| FORMAT | 0.0233 | 0 | 0 | 0 | 0.0032 | 0 | 0 | 0 | 0 | 0 | 0 | 0 | 0 | 0 | 0 | 0 | 0 | 0 | 0 |
| 1998CATA | 0.0447 | 0 | 0 | 0 | 0 | 0 | 0 | 0 | 0 | 0 | 0 | 0 | 0 | 0 | 0 | 0 | 0 | 0 | 0 |
| 1998CATB | 0.0403 | 0 | 0 | 0 | 0 | 0 | 0 | 0 | 0 | 0.0062 | 0 | 0 | 0 | 0 | 0 | 0 | 0.0044 | | |
| 1998CATC | 0.037 | 0 | 0 | 0.0033 | 0 | 0 | 0 | 0 | 0 | 0 | 0 | 0 | 0 | 0 | 0 | 0 | 0 | | |
| 1998CATD | 0.039 | 0 | 0 | 0 | 0.0042 | 0 | 0 | 0 | 0.0025 | 0 | 0 | 0 | 0 | 0 | 0 | 0 | 0.0054 | | |
| 1998CATE | 0.0373 | 0 | 0 | 0 | 0.0063 | 0 | 0 | 0 | 0.007 | 0 | 0.0043 | 0 | 0 | 0 | 0 | 0 | 0 | | |
| 1998CATF | 0.0404 | 0 | 0 | 0.0019 | 0.0058 | 0 | 0 | 0 | 0 | 0 | 0 | 0 | 0 | 0 | 0 | 0 | 0 | | |
| GBNA | 0.0374 | 0 | 0 | 0 | 0 | 0 | 0 | 0 | 0 | 0 | 0 | 0 | 0 | 0 | 0 | 0 | 0 | | |
| GBNB | 0.0373 | 0 | 0 | 0 | 0.0025 | 0 | 0 | 0 | 0 | 0 | 0 | 0 | 0 | 0 | 0 | 0 | 0 | | |
| GBNC | 0.0461 | 0 | 0 | 0.006 | 0 | 0 | 0 | 0 | 0 | 0 | 0 | 0 | 0 | 0 | 0 | 0 | 0 | | |
| GBND | 0.0447 | 0 | 0 | 0 | 0.0073 | 0 | 0 | 0 | 0 | 0 | 0 | 0 | 0 | 0 | 0 | 0 | 0 | | |
| GBNE | 0.0391 | 0 | 0.005 | 0 | 0 | 0 | 0 | 0 | 0 | 0 | 0.0066 | 0 | 0 | 0 | 0 | 0 | 0 | | |
| ECS 585G | 0.0378 | 0 | 0 | 0.0047 | 0.0062 | 0 | 0 | 0 | 0 | 0 | 0.0044 | 0 | 0 | 0 | 0 | 0 | 0 | | |
| ECS 585I | 0.0393 | 0.005 | 0 | 0 | 0.0052 | 0 | 0 | 0 | 0 | 0 | 0.0046 | 0 | 0 | 0 | 0 | 0 | 0 | | |
| ECS 585J | 0.0339 | 0.005 | 0 | 0 | 0.0063 | 0 | 0 | 0 | 0 | 0.0027 | 0.0047 | 0.0027 | 0 | 0 | 0 | 0 | 0 | | |
| ECS 585L | 0.0337 | 0.005 | 0 | 0 | 0.0056 | 0 | 0 | 0 | 0 | 0 | 0.0069 | 0 | 0 | 0 | 0 | 0 | 0 | | |
| KITCHEN SINK A | 0.0248 | 0.0025 | 0.0025 | 0 | 0.0038 | 0.004 | 0.0049 | 0 | 0.0012 | 0.0027 | 0.0026 | 0.0011 | 0.0003 | 0.0011 | 0.0019 | 0.0037 | 0.0007 | | |
| KITCHEN SINK C | 0.0261 | 0.0025 | 0.001 | 0.0032 | 0 | 0.0034 | 0.002 | 0 | 0.0013 | 0 | 0.0043 | 0.0011 | 0.0004 | 0.0011 | 0.0018 | 0.0033 | 0.0036 | | |
| IHSABI | 0.0432 | 0.0025 | 0 | 0 | 0.0036 | 0 | 0 | 0 | 0 | 0 | 0 | 0 | 0 | 0 | 0 | 0 | 0 | | |
| IHSABK | 0.0441 | 0 | 0 | 0.0025 | 0.0021 | 0 | 0 | 0 | 0 | 0 | 0 | 0 | 0 | 0 | 0 | 0 | 0 | | |
| IHSABM | 0.0453 | 0 | 0.0025 | 0 | 0.0038 | 0 | 0 | 0 | 0 | 0 | 0 | 0 | 0 | 0 | 0 | 0 | 0 | | |
| IHSABN | 0.0412 | 0.0025 | 0 | 0.004 | 0.0029 | 0 | 0 | 0 | 0 | 0 | 0 | 0 | 0 | 0 | 0 | 0 | 0 | | |
| | 0.05 | 0 | 0 | 0 | 0 | 0 | 0 | 0 | 0 | 0 | 0 | 0 | 0 | 0 | 0 | 0 | 0 | | |

FIG. 7B

| TOTAL WT | Cbs | N | S | NH3 | Fe | Rs | Rl | Fe3S | Fe2S | FeN | FeCl | CaN | CuN | CuCl | KNO3 | NaCl | MgS | Zn | Mn | P | U | KCl |
|---|---|---|---|---|---|---|---|---|---|---|---|---|---|---|---|---|---|---|---|---|---|---|
| 0.0488 | 0.0 | 0.0 | 0.0 | 0.0 | 0.0 | 0.0 | 0.0 | 0.0 | 0.0 | 100.0 | 0.0 | 0.0 | 0.0 | 0.0 | 0.0 | 0.0 | 0.0 | 0.0 | 0.0 | 0.0 | 0.0 | 0.0 |
| 0.049 | 0.0 | 20.4 | 0.0 | 0.0 | 0.0 | 0.0 | 0.0 | 0.0 | 0.0 | 79.6 | 0.0 | 0.0 | 0.0 | 0.0 | 0.0 | 0.0 | 0.0 | 0.0 | 0.0 | 0.0 | 0.0 | 0.0 |
| 0.0524 | 0.0 | 76.3 | 0.0 | 0.0 | 0.0 | 0.0 | 0.0 | 0.0 | 0.0 | 23.7 | 0.0 | 0.0 | 0.0 | 0.0 | 0.0 | 0.0 | 0.0 | 0.0 | 0.0 | 0.0 | 0.0 | 0.0 |
| 0.0499 | 11.8 | 10.0 | 0.0 | 0.0 | 0.0 | 0.0 | 0.0 | 0.0 | 0.0 | 78.2 | 0.0 | 0.0 | 0.0 | 0.0 | 0.0 | 0.0 | 0.0 | 0.0 | 0.0 | 0.0 | 0.0 | 0.0 |
| 0.0512 | 28.5 | 9.8 | 0.0 | 0.0 | 0.0 | 0.0 | 0.0 | 0.0 | 0.0 | 61.7 | 0.0 | 0.0 | 0.0 | 0.0 | 0.0 | 0.0 | 0.0 | 0.0 | 0.0 | 0.0 | 0.0 | 0.0 |
| 0.051 | 42.4 | 9.8 | 0.0 | 0.0 | 0.0 | 0.0 | 0.0 | 0.0 | 0.0 | 47.8 | 0.0 | 0.0 | 0.0 | 0.0 | 0.0 | 0.0 | 0.0 | 0.0 | 0.0 | 0.0 | 0.0 | 0.0 |
| 0.0549 | 17.1 | 0.0 | 0.0 | 0.0 | 0.0 | 0.0 | 0.0 | 0.0 | 0.0 | 60.8 | 0.0 | 0.0 | 0.0 | 0.0 | 0.0 | 0.0 | 0.0 | 0.0 | 0.0 | 0.0 | 22.0 | 0.0 |
| 0.0505 | 88.1 | 0.0 | 0.0 | 0.0 | 11.9 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 0.0526 | 86.9 | 4.8 | 0.0 | 0.0 | 8.4 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 0.0513 | 88.7 | 4.9 | 0.0 | 0.0 | 0.0 | 0.0 | 6.4 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 0.0535 | 89.5 | 0.0 | 0.0 | 4.7 | 0.0 | 0.0 | 5.8 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 0.0468 | 88.9 | 0.0 | 5.3 | 0.0 | 0.0 | 0.0 | 5.8 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 0.0508 | 77.8 | 4.9 | 0.0 | 0.0 | 6.7 | 0.0 | 7.1 | 0.0 | 0.0 | 0.0 | 0.0 | 0.0 | 0.0 | 0.0 | 3.5 | 0.0 | 0.0 | 0.0 | 0.0 | 0.0 | 0.0 | 0.0 |
| 0.0494 | 64.8 | 0.0 | 10.1 | 0.0 | 0.0 | 0.0 | 12.8 | 0.0 | 0.0 | 0.0 | 0.0 | 0.0 | 0.0 | 0.0 | 0.0 | 0.0 | 12.3 | 0.0 | 0.0 | 0.0 | 0.0 | 0.0 |
| 0.0485 | 64.5 | 10.3 | 0.0 | 0.0 | 0.0 | 0.0 | 11.3 | 0.0 | 0.0 | 0.0 | 0.0 | 13.8 | 0.0 | 0.0 | 0.0 | 0.0 | 0.0 | 0.0 | 0.0 | 0.0 | 0.0 | 0.0 |
| 0.044 | 52.7 | 0.0 | 0.0 | 0.0 | 0.0 | 0.0 | 0.0 | 47.3 | 0.0 | 0.0 | 0.0 | 0.0 | 0.0 | 0.0 | 0.0 | 0.0 | 0.0 | 0.0 | 0.0 | 0.0 | 0.0 | 0.0 |
| 0.0492 | 49.4 | 0.0 | 0.0 | 0.0 | 0.0 | 0.0 | 0.0 | 0.0 | 50.6 | 0.0 | 0.0 | 0.0 | 0.0 | 0.0 | 0.0 | 0.0 | 0.0 | 0.0 | 0.0 | 0.0 | 0.0 | 0.0 |
| 0.0484 | 48.1 | 0.0 | 0.0 | 0.0 | 0.0 | 0.0 | 0.0 | 0.0 | 0.0 | 51.9 | 0.0 | 0.0 | 0.0 | 0.0 | 0.0 | 0.0 | 0.0 | 0.0 | 0.0 | 0.0 | 0.0 | 0.0 |
| 0.0526 | 47.1 | 0.0 | 0.0 | 0.0 | 0.0 | 0.0 | 0.0 | 0.0 | 0.0 | 0.0 | 52.9 | 0.0 | 0.0 | 0.0 | 0.0 | 0.0 | 0.0 | 0.0 | 0.0 | 0.0 | 0.0 | 0.0 |
| 0.0468 | 50.9 | 0.0 | 0.0 | 0.0 | 49.1 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |

| ELEMENT | ROOM TEMP HEATER ohm | ROOM TEMP SENSOR ohm | AFTER B V | AFTER B I | WATTS | AFTER B ohm SENSOR | AFTER B SENSOR TEMP | AFTER B V | AFTER B I | WATTS | AFTER B ohm SENSOR | AFTER B TEMP | AFTER B V | AFTER B I | WATTS | AFTER B ohm SENSOR | AFTER B TEMP | COMMENTS | RANK B 700 | ELEMENT | AFTER B ohm SENSOR 700 |
|---|---|---|---|---|---|---|---|---|---|---|---|---|---|---|---|---|---|---|---|---|---|
| FN1 | 5.4 | 9.90E+06 | 3.7 | 0.4 | 1.48 | 9.34E+06 | 294 | 5 | 0.47 | 2.35 | 7.40E+05 | 434 | 7.7 | 0.55 | 4.235 | 2.60E-04 | 704 | | 30 | FN8 | 3.00E+06 |
| FN2 | 5.2 | 1.06E+07 | 3.7 | 0.4 | 1.48 | 1.06E+07 | 297 | 5 | 0.47 | 2.35 | 3.80E+06 | 465 | 7.2 | 0.55 | 3.96 | 1.25E-05 | 714 | | 18 | FN7 | 2.60E+06 |
| FN5 | 5.2 | 1.17E+07 | 4.3 | 0.38 | 1.634 | 1.15E+07 | 296 | 5 | 0.45 | 2.25 | 1.04E+07 | 341 | 7.7 | 0.54 | 4.158 | 1.31E-05 | 688 | BAD CONNECTION | 16 | ECS 869d | 2.40E+06 |
| FN6 | 5.4 | 6.50E+01 | 4.1 | 0.37 | 1.517 | 3.40E+02 | 294 | 5 | 0.45 | 2.25 | 3.05E+02 | 382 | 7.1 | 0.52 | 3.692 | 1.20E-05 | 696 | 700 SLOW TO ST | 19 | ECS 585e | 2.40E+06 |
| FN7 | 5.4 | 2.12E+02 | 4 | 0.37 | 1.48 | 1.18E+07 | 302 | 5 | 0.43 | 2.15 | 1.14E+07 | 398 | 7.7 | 0.54 | 4.158 | 2.60E-06 | 698 | | 2 | IHSABf | 2.00E+06 |
| FN8 | 5.3 | 6.60E+02 | 4.4 | 0.4 | 1.76 | 1.25E+06 | 310 | 5 | 0.43 | 2.15 | 1.11E+06 | 385 | 7.8 | 0.54 | 4.212 | 3.00E-06 | 705 | | 1 | IHSABb | 1.00E+06 |
| FN10 | 5.2 | 1.30E+00 | 4.3 | 0.4 | 1.72 | 1.16E+07 | 291 | 5 | 0.45 | 2.25 | 1.13E+07 | 381 | 7.3 | 0.55 | 4.015 | 9.20E-05 | 700 | | 8 | 1998CATe | 1.00E+06 |
| ECS 869b | 5.3 | 4.50E+00 | 4.6 | 0.4 | 1.84 | 5.70E+04 | 303 | 5 | 0.43 | 2.15 | 4.70E+04 | 394 | 7.8 | 0.56 | 4.368 | 9.40E-04 | 705 | | 23 | FN10 | 9.20E+05 |
| ECS 869d | 5.4 | 2.40E+02 | 3.7 | 0.35 | 1.295 | 5.70E+04 | 306 | 5 | 0.48 | 2.4 | 4.40E+04 | 436 | 7.2 | 0.56 | 4.032 | 2.40E-06 | 703 | | 3 | IHSABg | 5.80E+05 |
| IHSABb | 5.5 | 1.67E+02 | 4.5 | 0.4 | 1.8 | 4.40E+03 | 307 | 5 | 0.44 | 2.2 | 3.80E+03 | 337 | 7.8 | 0.56 | 4.368 | 1.00E-06 | 704 | 700 SLOW TO ST | 6 | ECS 585a | 4.88E+05 |
| IHSABd | 5.4 | 1.26E+02 | 4.2 | 0.4 | 1.68 | 2.20E+02 | 280 | 5 | 0.44 | 2.2 | 1.95E+02 | 375 | 7.6 | 0.57 | 4.332 | 2.80E-02 | 695 | | 39 | FORMc | 4.50E+05 |
| IHSABf | 5.3 | 3.40E+03 | 4.5 | 0.42 | 1.89 | 1.09E+07 | 303 | 5 | 0.46 | 2.3 | 1.07E+07 | 370 | 7.9 | 0.58 | 4.582 | 2.00E-06 | 707 | | 5 | SINKc | 3.60E+05 |
| IHSABg | 5.6 | 9.80E+03 | 4.4 | 0.39 | 1.716 | 2.50E+06 | 292 | 5 | 0.44 | 2.2 | 2.20E+06 | 344 | 8.1 | 0.56 | 4.536 | 5.80E-05 | 690 | | 9 | 1998CATa | 3.00E+05 |
| ECS 585a | 5.1 | 4.00E+01 | 3.8 | 0.39 | 1.482 | 1.22E+05 | 315 | 5 | 0.46 | 2.3 | 8.30E+04 | 462 | 7 | 0.55 | 3.85 | 4.88E-05 | 692 | | 10 | FORMe | 1.95E+05 |
| ECS 585e | 5.4 | 1.24E+02 | 4.3 | 0.4 | 1.72 | 2.30E+06 | 295 | 5 | 0.47 | 2.35 | 1.90E+06 | 371 | 8 | 0.56 | 4.48 | 2.40E-06 | 713 | | 4 | 1998CATc | 1.70E+05 |
| FORMb | 5.4 | 7.60E+01 | 4.2 | 0.39 | 1.638 | 5.10E+06 | 294 | 5 | 0.44 | 2.2 | 2.10E+06 | 382 | 7.7 | 0.56 | 4.312 | 6.00E-04 | 700 | | 25 | FN5 | 1.31E+05 |
| FORMc | 5.4 | 2.30E+03 | 4 | 0.39 | 1.56 | 1.16E+07 | 314 | 5 | 0.44 | 2.2 | 1.06E+07 | 387 | 7.6 | 0.57 | 4.322 | 4.50E-05 | 705 | | 11 | SINKg | 1.30E+05 |

| RANK B 300 | | ELEMENT | AFTER B ohm SENSOR 300 |
|---|---|---|---|
| FN1 | 16 | FN7 | 1.18E+07 |
| FN2 | 11 | FN10 | 1.16E+07 |
| FN5 | 4 | FORMc | 1.16E+07 |
| FN6 | 38 | FN5 | 1.15E+07 |
| FN7 | 1 | 1998CATe | 1.12E+07 |
| FN8 | 24 | SINK a | 1.12E+07 |
| FN10 | 2 | 1998 CATc | 1.10E+07 |
| ECS 869b | 30 | IHSABf | 1.09E+07 |
| ECS 869d | 31 | ECS 585j | 1.09E+07 |
| IHSABb | 33 | 1998 CATb | 1.08E+07 |
| IHSABd | 39 | FN2 | 1.06E+07 |
| IHSABf | 8 | 1998CATa | 1.05E+07 |
| IHSABg | 21 | SINK c | 1.04E+07 |
| ECS 585a | 28 | ECS 585g | 1.00E+07 |
| ECS 585e | 22 | ECS 585i | 9.40E+06 |
| FORMb | 20 | FN1 | 9.34E+06 |
| FORMc | 3 | FORMe | 9.10E+06 |
| FORMe | 17 | ECS 585l | 8.80E+06 |
| FORMf | 29 | GENe | 8.30E+06 |
| FORMg | 23 | FORMb | 5.10E+06 |
| FORMi | 27 | IHSABb | 2.50E+06 |
| 1998CATa | 12 | ECS 585e | 2.30E+06 |
| 1998 CATb | 10 | FORMg | 1.30E+06 |
| 1998 CATc | 7 | FN8 | 1.25E+06 |
| 1998CATd | 37 | GENa | 8.70E+05 |
| 1998CATe | 5 | GENc | 6.50E+05 |
| 1998CATf | 32 | FORMi | 5.00E+05 |
| GENa | 25 | ECS 585a | 1.22E+05 |
| GENb | 36 | FORMf | 7.50E+04 |
| GENc | 26 | ECS 869b | 5.70E+04 |
| GENd | 34 | ECS 869d | 5.70E+04 |
| GENe | 19 | 1998CATf | 1.94E+04 |
| ECS 585g | 14 | IHSABb | 4.40E+03 |
| ECS 585i | 15 | GENd | 1.50E+03 |
| ECS 585j | 9 | C | 1.25E+03 |
| ECS 585l | 18 | GENb | 8.66E+02 |
| SINK a | 6 | 1998CATd | 5.80E+02 |
| SINK c | 13 | FN6 | 3.40E+02 |
| C | 35 | IHSABd | 2.20E+02 |

FIG. 9C

| ELEMENT | ROOM TEMP HEATER ohm | ROOM TEMP SENSOR ohm | AFTER C V | AFTER C1 | AFTER WATTS | AFTER C ohm SENSOR | AFTER C TEMP | AFTER C V | AFTER C1 | AFTER WATTS | AFTER C ohm SENSOR | AFTER C TEMP | COMMENTS | RANK C 700 | ELEMENT 700 | AFTER C ohm SENSOR 700 |
|---|---|---|---|---|---|---|---|---|---|---|---|---|---|---|---|---|
| FN1 | 5.2 | 6.00E+06 | 4.3 | 0.4 | 1.72 | 5.50E+06 | 300 | 8.2 | 0.6 | 4.92 | 1.10E+04 | 695 | | 35 | ECS 585e | 6.10E+07 |
| FN2 | 5.5 | 5.50E+06 | 4.6 | 0.4 | 1.84 | 5.10E+06 | 300 | 7.6 | 0.6 | 4.56 | 3.10E+04 | 710 | | 34 | IHSABb | 1.58E+07 |
| FN5 | 5.2 | 4.30E+06 | 3.7 | 0.4 | 1.48 | 4.10E+06 | 300 | 7.3 | 0.6 | 4.38 | 2.75E+05 | 700 | | 27 | ECS 585q | 1.05E+07 |
| FN6 | 5.5 | 3.10E+06 | 4.5 | 0.4 | 1.8 | 3.10E+06 | 285 | 7.9 | 0.6 | 4.74 | 3.22E+05 | 700 | | 26 | ECS 869d | 6.90E+06 |
| FN7 | 5.6 | 7.70E+06 | 4.3 | 0.4 | 1.72 | 7.60E+06 | 295 | 8 | 0.6 | 4.8 | 6.40E+06 | 704 | | 5 | FN7 | 6.40E+06 |
| FN8 | 5.6 | 4.10E+06 | 3.7 | 0.4 | 1.48 | 4.00E+06 | 300 | 7 | 0.6 | 4.2 | 3.10E+06 | 700 | | 10 | 1998CATf | 5.60E+06 |
| FN10 | 5.2 | 6.40E+06 | 4.4 | 0.4 | 1.76 | 6.20E+06 | 293 | 7.5 | 0.6 | 4.5 | 5.70E+06 | 692 | | 17 | 1998CATq | 4.40E+06 |
| ECS 869b | 5.9 | 6.50E+06 | 3.7 | 0.4 | 1.48 | 6.30E+06 | 300 | 7.3 | 0.6 | 4.38 | 5.80E+05 | 703 | | 19 | GFMb | 4.30E+06 |
| ECS 869d | 5.2 | 9.10E+06 | 3.8 | 0.4 | 1.52 | 8.90E+06 | 288 | 7.2 | 0.6 | 4.32 | 6.90E+06 | 703 | | 4 | GFMk | 3.60E+06 |
| IHSABb | 5.4 | 2.05E+07 | 3.6 | 0.4 | 1.44 | 2.00E+07 | 303 | 7.3 | 0.6 | 4.38 | 1.58E+07 | 698 | | 2 | FN8 | 3.10E+06 |
| IHSABd | 5.3 | 3.00E+08 | 4.3 | 0.4 | 1.72 | 2.80E+06 | 290 | 8 | 0.6 | 4.8 | 2.40E+06 | 700 | | 12 | GFMd | 3.00E+06 |
| IHSABf | 5.2 | 2.60E+06 | 4.8 | 0.4 | 1.92 | 2.50E+06 | 295 | 8 | 0.6 | 4.8 | 1.90E+06 | 697 | | 14 | IHSABd | 2.40E+06 |
| IHSABg | 5.5 | 4.00E+07 | 3.9 | 0.4 | 1.56 | 3.80E+06 | 303 | 8 | 0.6 | 4.8 | 2.00E+06 | 709 | | 13 | IHSABg | 2.00E+06 |
| ECS 585a | 5.1 | 3.40E+07 | 3.6 | 0.4 | 1.44 | 3.60E+07 | 310 | 7.2 | 0.6 | 4.32 | 1.05E+07 | 701 | 30X MAG | 3 | IHSABf | 1.90E+06 |
| ECS 585q | 5.2 | 1.10E+08 | 3.4 | 0.4 | 1.36 | 1.10E+08 | 290 | 6.9 | 0.6 | 4.14 | 6.10E+07 | 711 | 30X MAG | 1 | GFMe | 1.60E+06 |
| FORMb | 5.3 | 1.30E+08 | 3.7 | 0.4 | 1.48 | 1.40E+07 | 290 | 7.2 | 0.6 | 4.32 | 4.60E+04 | 712 | 30X MAG | 33 | IHSABn | 1.50E+06 |
| FORMc | 5.5 | 1.58E+07 | 4 | 0.4 | 1.6 | 9.60E+06 | 303 | 7.7 | 0.6 | 4.62 | 1.35E+05 | 707 | | 30 | FN10 | 9.00E+05 |

| RANK B 300 | ELEMENT | AFTER B ohm SENSOR 300 |
|---|---|---|
| 1 | FN1 | |
| 2 | FN2 | |
| 3 | FN5 | |
| 4 | FN6 | |
| 5 | FN7 | |
| 6 | FN8 | |
| 7 | FN10 | |
| 8 | ECS 869b | |
| 9 | ECS 869d | |
| 10 | IHSABb | |
| 11 | IHSABd | |
| 12 | IHSABf | |
| 13 | IHSABg | |
| 14 | ECS 585a | |
| 15 | ECS 585e | |
| 16 | FORMb | |
| 17 | FORMc | |
| 18 | FORMe | |
| 19 | FORMf | |
| 20 | FORMg | |
| 21 | FORMi | |
| 22 | 1998CATa | |
| 23 | 1998CATb | |
| 24 | 1998CATc | |
| 25 | 1998CATd | |
| 26 | 1998CATe | |
| 27 | 1998CATf | |
| 28 | GENa | |
| 29 | GENb | |
| 30 | GENc | |
| 31 | GENd | |
| 32 | GENe | |
| 33 | ECS 585g | |
| 34 | ECS 585i | |
| 35 | ECS 585j | |
| 36 | ECS 585l | |
| 37 | SINK a | |
| 38 | SINK c | |
| 39 | C | |
| 40 | IHSABi | |
| 41 | IHSABk | |
| 42 | IHSABm | |
| 43 | IHSABn | |

FIG. 10C

| ELEMENT | FIGURE | ROOM TEMP SENSOR ohm | AFTER AV | AFTER A1 | WATTS | AFTER A ohm SENSOR | AFTER A TEMP | AFTER A AV | AFTER A1 | WATTS | AFTER A ohm SENSOR | AFTER A TEMP | AFTER A AV | AFTER A1 | WATTS | AFTER A ohm SENSOR | AFTER A TEMP |
|---|---|---|---|---|---|---|---|---|---|---|---|---|---|---|---|---|---|
| FN1 |  | 1.126E+07 | 3.6 | 0.43 | 1.548 | 1.13E-07 | 310 | 5 | 0.5 | 2.5 | 1.11E-07 | 486 | 6.7 | 0.55 | 3.685 | 5.22E-06 | 689 |
| FN2 | 29 | 1.090E+07 | 3.6 | 0.45 | 1.62 | 9.50E-06 | 300 | 5 | 0.52 | 2.6 | 4.10E-06 | 498 | 6.7 | 0.56 | 3.752 | 2.20E-05 | 698 |
| FN5 | 30 | 1.116E+07 | 3.5 | 0.42 | 1.47 | 1.12E-07 | 300 | 5 | 0.49 | 2.45 | 1.10E+07 | 497 | 6.3 | 0.54 | 3.402 | 8.59E-06 | 682 |
| FN6 |  | 5.300E+01 | 3.4 | 0.42 | 1.428 | 3.14E+01 | 350 | 5 | 0.49 | 2.45 | 3.32E+01 | 570 | 6.2 | 0.53 | 3.286 | 1.00E-05 | 700 |
| FN7 | 37 | 7.300E+01 | 3.4 | 0.45 | 1.53 | 5.60E+01 | 320 | 5 | 0.52 | 2.6 | 5.80E+01 | 500 | 6.3 | 0.53 | 3.339 | 4.90E-06 | 655 |
| FN8 | 38 | 4.800E+01 | 3.3 | 0.41 | 1.353 | 5.00E+01 | 302 | 5 | 0.53 | 2.65 | 5.10E+01 | 514 | 6.3 | 0.53 | 3.339 | 5.10E-06 | 690 |
| FN10 |  | 8.000E+01 | 3.3 | 0.42 | 1.386 | 5.70E+01 | 294 | 5 | 0.53 | 2.65 | 4.60E+01 | 520 | 6.3 | 0.55 | 3.465 | 6.30E-01 | 700 |
| ECS 869b | 26 | 2.700E+01 | 3.3 | 0.42 | 1.386 | 2.90E+01 | 335 | 5 | 0.5 | 2.5 | 3.10E+01 | 595 | 6 | 0.52 | 3.12 | 1.11E-05 | 666 |
| ECS 869d | 27 | 1.380E+02 | 3.3 | 0.42 | 1.386 | 8.30E-01 | 304 | 5 | 0.53 | 2.65 | 7.20E+01 | 530 | 6.5 | 0.56 | 3.64 | 1.00E-06 | 670 |
| IHSABd | 28 | 9.500E+05 | 3.6 | 0.41 | 1.476 | 3.80E+04 | 288 | 5 | 0.48 | 2.4 | 6.60E+04 | 500 | 6.7 | 0.54 | 3.618 | 7.10E-06 | 707 |
| IHSAB9 | 9 | 1.030E+02 | 3.5 | 0.43 | 1.505 | 7.70E+01 | 330 | 5 | 0.52 | 2.6 | 6.10E+01 | 532 | 6.3 | 0.54 | 3.402 | 2.00E-02 | 715 |
| IHSAB7 | 16 | 5.900E+01 | 3.5 | 0.41 | 1.435 | 4.80E+01 | 333 | 5 | 0.49 | 2.45 | 4.50E+01 | 527 | 6.6 | 0.55 | 3.63 | 1.30E-06 | 703 |
| IHSAB9 |  | 2.800E+01 | 3.4 | 0.4 | 1.36 | 3.20E-01 | 345 | 5 | 0.49 | 2.45 | 3.30E+01 | 560 | 6.4 | 0.54 | 3.456 | 6.30E-01 | 715 |
| ECS 585a | 15 | 5.700E+01 | 3.4 | 0.48 | 1.632 | 4.60E+01 | 270 | 5 | 0.52 | 2.6 | 4.40E+01 | 540 | 6.4 | 0.54 | 3.456 | 2.80E+02 | 700 |
| ECS 585e | 32 | 1.860E+02 | 3.5 | 0.4 | 1.4 | 8.80E+01 | 295 | 5 | 0.5 | 2.5 | 6.20E+01 | 495 | 7.4 | 0.55 | 4.07 | 2.30E-06 | 703 |
| FORMb | 13 | 1.440E+02 | 3.5 | 0.42 | 1.47 | 4.60E+01 | 310 | 5 | 0.5 | 2.5 | 4.80E+01 | 520 | 6.7 | 0.54 | 3.618 | 4.45E-05 | 710 |
| FORMc | 14 | 1.370E+02 | 3.5 | 0.41 | 1.435 | 7.20E+01 | 307 | 5 | 0.49 | 2.45 | 6.60E+01 | 505 | 6.7 | 0.54 | 3.618 | 5.50E-05 | 700 |

FIG. 11A

| | | | | | | | | | | | | | | | | |
|---|---|---|---|---|---|---|---|---|---|---|---|---|---|---|---|---|
| FORMe | | 2.70E+01 | 3.4 | 0.4 | 1.36 | 3.30E+01 | 286 | 5 | 0.48 | 2.4 | 3.60E+01 | 500 | 6.5 | 0.54 | 3.51 | 4.75E+05 | 681 |
| FORMf | | 5.10E+01 | 3.5 | 0.41 | 1.435 | 3.60E+01 | 303 | 5 | 0.49 | 2.4 | 3.50E+01 | 505 | 6.7 | 0.54 | 3.618 | 1.50E+05 | 713 |
| FORMg | | 1.43E+02 | 3.4 | 0.4 | 1.36 | 9.50E+01 | 298 | 5 | 0.5 | 2.5 | 6.00E+01 | 475 | 6.9 | 0.55 | 3.795 | 6.00E+03 | 730 |
| FORMi | | 1.70E+02 | 3.5 | 0.39 | 1.292 | 1.15E+02 | 324 | 5 | 0.48 | 2.4 | 8.40E+01 | 526 | 6.4 | 0.54 | 3.456 | 2.50E+02 | 684 |
| FORMj | | 6.60E+01 | 3.9 | 0.4 | 1.56 | 4.60E+01 | 287 | 5 | 0.48 | 2.4 | 4.30E+01 | 447 | 7.2 | 0.55 | 3.96 | 4.00E+06 | 715 |
| 1998CATa | 25 | 3.10E+01 | 3.5 | 0.42 | 1.638 | 3.00E+01 | 340 | 5 | 0.5 | 2.5 | 3.10E+01 | 465 | 6.4 | 0.52 | 3.328 | 1.15E+05 | 678 |
| 1998CATb | 31 | 1.96E+02 | 3.5 | 0.43 | 1.505 | 1.07E+02 | 320 | 5 | 0.52 | 2.6 | 1.50E+04 | 555 | 6.6 | 0.56 | 3.696 | 6.00E+05 | 711 |
| 1998CATc | | 1.82E+02 | 3.5 | 0.42 | 1.47 | 1.20E+02 | 324 | 5 | 0.51 | 2.55 | 1.04E+02 | 504 | 6.6 | 0.57 | 3.762 | 2.90E+03 | 708 |
| 1998CATd | 23 | 1.03E+03 | 3.5 | 0.42 | 1.47 | 4.00E+02 | 292 | 5 | 0.49 | 2.45 | 4.50E+02 | 495 | 6.8 | 0.56 | 3.808 | 2.50E+05 | 732 |
| 1998CATe | 17 | 3.10E+02 | 3.4 | 0.4 | 1.4 | 1.30E+02 | 290 | 5 | 0.52 | 2.6 | 5.00E+03 | 470 | 7 | 0.56 | 3.92 | 2.80E+03 | 705 |
| 1998CATf | 24 | 4.70E+02 | 3.4 | 0.41 | 1.394 | 3.90E+02 | 330 | 5 | 0.5 | 2.5 | 4.00E+01 | 530 | 6.7 | 0.55 | 3.685 | 9.50E+04 | 720 |
| GENa | 12 | 9.60E+02 | 3.4 | 0.41 | 1.394 | 6.90E+02 | 300 | 5 | 0.49 | 2.45 | 5.30E+01 | 528 | 6.5 | 0.55 | 3.575 | 1.30E+02 | 710 |
| GENb | 11 | 1.17E+02 | 3.6 | 0.42 | 1.512 | 8.20E+01 | 315 | 5 | 0.5 | 2.5 | 6.60E+01 | 508 | 6.7 | 0.54 | 3.618 | 2.50E+02 | 714 |
| GENc | | 3.67E+02 | 3.4 | 0.39 | 1.326 | 2.11E+02 | 324 | 5 | 0.53 | 2.65 | 1.57E+02 | 520 | 6.3 | 0.52 | 3.276 | 7.50E+02 | 705 |
| GENd | 18 | 1.10E+02 | 3.7 | 0.42 | 1.554 | 6.50E+01 | 303 | 5 | 0.51 | 2.55 | 5.60E+01 | 480 | 6.7 | 0.54 | 3.618 | 1.00E+05 | 690 |
| GENe | 19 | 5.50E+01 | 3.4 | 0.4 | 1.36 | 4.40E+01 | 292 | 5 | 0.52 | 2.6 | 3.70E+01 | 497 | 6.8 | 0.55 | 3.74 | 1.00E+05 | 703 |
| ECS 5a | 20 | 7.70E+01 | 3.4 | 0.4 | 1.36 | 4.40E+01 | 320 | 5 | 0.51 | 2.55 | 4.00E+01 | 517 | 6.7 | 0.54 | 3.618 | 1.80E+05 | 717 |
| ECS 5b | 21 | 4.30E+01 | 3.5 | 0.41 | 1.435 | 3.30E+01 | 312 | 5 | 0.51 | 2.55 | 3.30E+01 | 503 | 6.6 | 0.54 | 3.564 | 1.25E+05 | 688 |
| ECS 5c | 22 | 4.30E+01 | 3.4 | 0.4 | 1.36 | 4.00E+01 | 330 | 5 | 0.52 | 2.6 | 4.00E+01 | 533 | 6.5 | 0.54 | 3.51 | 1.60E+05 | 695 |
| ECS 5d | | 1.18E+02 | 3.5 | 0.42 | 1.47 | 5.80E+01 | 325 | 5 | 0.54 | 2.7 | 5.00E+01 | 522 | 6.5 | 0.54 | 3.51 | 2.40E+06 | 715 |
| SINK a | | 5.20E+01 | 3.6 | 0.42 | 1.512 | 4.50E+01 | 314 | 5 | 0.52 | 2.6 | 4.10E+01 | 525 | 6.6 | 0.54 | 3.564 | 1.00E+05 | 708 |
| SINK c | 8 | | | | | | | | | | | | | | | | |
| IHSABi | 33 | | | | | | | | | | | | | | | | |
| IHSABk | 34 | | | | | | | | | | | | | | | | |
| IHSABm | 35 | | | | | | | | | | | | | | | | |
| IHSABn | 36 | | | | | | | | | | | | | | | | |

FIG. 11B

| ELEMENT | ROOM TEMP HEATER ohm | ROOM TEMP SENSOR ohm | AFTER BV | AFTER B1 | WATTS | AFTER B ohm SENSOR | AFTER B TEMP | AFTER B BV | AFTER B B1 | WATTS | AFTER B ohm SENSOR | AFTER B TEMP | AFTER B BV | AFTER B B1 | WATTS | AFTER B ohm SENSOR | AFTER B TEMP |
|---|---|---|---|---|---|---|---|---|---|---|---|---|---|---|---|---|---|
| FM1 | 5.4 | 2.90E+06 | 3.7 | 0.4 | 1.48 | 9.34E+06 | 294 | 5 | 0.47 | 2.35 | 7.40E+05 | 434 | 7.7 | 0.55 | 4.235 | 2.60E+04 | 704 |
| FM2 | 5.2 | 1.06E+07 | 3.7 | 0.4 | 1.48 | 1.06E+07 | 297 | 5 | 0.47 | 2.35 | 3.80E+06 | 465 | 7.2 | 0.55 | 3.96 | 1.25E+05 | 714 |
| FM5 | 5.2 | 1.17E+07 | 4.3 | 0.38 | 1.634 | 1.15E+07 | 296 | 5 | 0.45 | 2.25 | 1.04E+07 | 341 | 7.7 | 0.54 | 4.158 | 1.31E+05 | 688 |
| FM6 | 5.4 | 6.50E+01 | 4.1 | 0.37 | 1.517 | 3.40E+02 | 294 | 5 | 0.45 | 2.25 | 3.05E+02 | 382 | 7.1 | 0.52 | 3.692 | 1.20E+05 | 696 |
| FM7 | 5.4 | 2.12E+02 | 4 | 0.37 | 1.48 | 1.18E+07 | 302 | 5 | 0.43 | 2.15 | 1.14E+07 | 398 | 7.7 | 0.54 | 4.158 | 2.60E+06 | 698 |
| FM8 | 5.3 | 6.60E+02 | 4.4 | 0.4 | 1.76 | 1.25E+06 | 310 | 5 | 0.43 | 2.15 | 1.11E+06 | 385 | 7.8 | 0.54 | 4.212 | 3.00E+06 | 705 |
| FM10 | 5.2 | 1.30E+00 | 4.3 | 0.4 | 1.72 | 1.16E+07 | 291 | 5 | 0.45 | 2.25 | 1.13E+07 | 381 | 7.3 | 0.55 | 4.015 | 9.20E+05 | 700 |
| ECS 869b | 5.3 | 4.50E+00 | 4.6 | 0.4 | 1.84 | 5.70E+04 | 303 | 5 | 0.43 | 2.15 | 4.70E+04 | 394 | 7.8 | 0.56 | 4.368 | 9.40E+04 | 705 |
| ECS 869d | 5.3 | 2.40E+02 | 3.7 | 0.35 | 1.295 | 5.70E+04 | 306 | 5 | 0.48 | 2.4 | 4.40E+04 | 436 | 7.2 | 0.56 | 4.032 | 2.40E+06 | 703 |
| THSABb | 5.5 | 1.67E+02 | 4.5 | 0.4 | 1.8 | 4.40E+03 | 307 | 5 | 0.44 | 2.2 | 3.80E+03 | 337 | 7.8 | 0.56 | 4.368 | 1.00E+06 | 704 |
| THSABd | 5.4 | 1.26E+02 | 4.2 | 0.4 | 1.68 | 2.20E+02 | 280 | 5 | 0.44 | 2.2 | 1.95E+02 | 375 | 7.6 | 0.57 | 4.332 | 2.80E+05 | 695 |
| THSABf | 5.3 | 3.40E+03 | 4.5 | 0.42 | 1.89 | 1.09E+07 | 303 | 5 | 0.46 | 2.3 | 1.07E+07 | 370 | 7.9 | 0.58 | 4.582 | 2.00E+06 | 707 |
| THSABg | 5.6 | 9.80E+03 | 4.4 | 0.39 | 1.716 | 2.50E+06 | 292 | 5 | 0.44 | 2.2 | 2.20E+06 | 344 | 8.1 | 0.56 | 4.536 | 5.80E+05 | 690 |
| ECS 585a | 5.1 | 4.00E+01 | 3.8 | 0.39 | 1.482 | 1.22E+05 | 315 | 5 | 0.46 | 2.3 | 8.30E+04 | 462 | 7 | 0.55 | 3.85 | 4.80E+05 | 692 |
| ECS 585e | 5.4 | 1.24E+02 | 4.3 | 0.4 | 1.72 | 2.30E+06 | 295 | 5 | 0.47 | 2.35 | 1.90E+06 | 371 | 8 | 0.56 | 4.48 | 2.40E+06 | 713 |
| FORMb | 5.4 | 7.60E+01 | 4.2 | 0.39 | 1.638 | 5.10E+06 | 294 | 5 | 0.44 | 2.2 | 2.10E+06 | 382 | 7.7 | 0.56 | 4.312 | 6.00E+04 | 700 |
| FORMc | 5.4 | 2.30E+03 | 4 | 0.39 | 1.56 | 1.16E+07 | 314 | 5 | 0.44 | 2.2 | 1.06E+07 | 387 | 7.6 | 0.57 | 4.332 | 4.50E+05 | 705 |

FIG. 11C

| | | | | | | | | | | | | | |
|---|---|---|---|---|---|---|---|---|---|---|---|---|---|
| FORMe | 5.5 | 8.40E+02 | 4.1 | 0.38 | 1.538 | 9.10E+06 | 300 | 5 | 0.45 | 2.25 | 4.20E+06 | 375 | 8 | 0.56 | 4.48 | 1.95E+05 | 704 |
| FORMf | 5.5 | 7.30E+01 | 3.6 | 0.38 | 1.368 | 7.50E+04 | 220 | 5 | 0.48 | 2.4 | 4.10E+04 | 436 | 7.5 | 0.57 | 4.275 | 1.00E+05 | 705 |
| FORMg | 5.7 | 1.85E+02 | 5 | 0.43 | 2.15 | 1.30E+06 | 312 | 5 | 0.43 | 2.15 | 1.30E+06 | 312 | 8.2 | 0.57 | 4.674 | 1.01E+05 | 714 |
| FORMi | 5.5 | 3.70E+01 | 4.7 | 0.39 | 1.833 | 5.00E+05 | 285 | 5 | 0.4 | 2 | 5.45E+02 | 340 | 7.8 | 0.54 | 4.212 | 9.00E+02 | 690 |
| 1998CATa | 5.8 | 1.33E+02 | 4.2 | 0.41 | 1.722 | 1.05E+07 | 320 | 5 | 0.39 | 1.95 | 8.00E+06 | 413 | 7.5 | 0.55 | 4.125 | 3.00E+05 | 705 |
| 1998 CATb | 5.6 | 7.40E+01 | 3.8 | 0.39 | 1.482 | 1.00E+07 | 300 | 5 | 0.47 | 2.35 | 7.10E+06 | 430 | 7.3 | 0.55 | 4.015 | 8.80E+04 | 708 |
| 1998 CATc | 5.2 | 3.45E+02 | 4.1 | 0.4 | 1.64 | 1.10E+07 | 287 | 5 | 0.42 | 2.1 | 7.80E+06 | 420 | 7.6 | 0.57 | 4.332 | 1.70E+05 | 706 |
| 1998 CATd | 5 | 1.86E+02 | 4 | 0.38 | 1.52 | 5.80E+02 | 288 | 5 | 0.47 | 2.35 | 4.30E+02 | 421 | 7.4 | 0.56 | 4.144 | 4.00E+02 | 700 |
| 1998 CATe | 5.4 | 4.70E+05 | 4.5 | 0.41 | 1.845 | 1.12E+07 | 316 | 5 | 0.46 | 2.3 | 1.00E+07 | 330 | 7.7 | 0.55 | 4.235 | 1.00E+06 | 693 |
| 1998 CATf | 5.3 | 1.10E+04 | 4.8 | 0.43 | 2.064 | 1.94E+04 | 301 | 5 | 0.4 | 2 | 1.20E+04 | 405 | 7.9 | 0.58 | 4.582 | 6.50E+03 | 691 |
| GENa | 5.4 | 3.40E+01 | 4.1 | 0.39 | 1.599 | 8.70E+05 | 308 | 5 | 0.4 | 2 | 6.20E+05 | 418 | 7.3 | 0.55 | 4.015 | 1.07E+05 | 704 |
| GENb | 5.2 | 3.63E+02 | 4 | 0.38 | 1.52 | 8.66E+02 | 300 | 5 | 0.47 | 2.35 | 7.15E+02 | 385 | 7.4 | 0.56 | 4.144 | 2.90E+03 | 707 |
| GENc | 5.6 |  | 5 | 0.44 | 2.2 | 6.50E+05 | 300 | 5 | 0.44 | 2.2 | 6.50E+05 | 300 | 7.6 | 0.56 | 4.256 | 3.50E+04 | 692 |
| GENd | 5.6 | 2.50E+03 | 3.7 | 0.4 | 1.48 | 1.30E+03 | 307 | 5 | 0.5 | 2.5 | 1.20E+03 | 415 | 7.8 | 0.6 | 4.68 | 1.20E+03 | 703 |
| GENe | 5.7 | 1.37E+02 | 3.6 | 0.4 | 1.44 | 8.30E+06 | 300 | 5 | 0.5 | 2.5 | 1.60E+06 | 430 | 7.3 | 0.6 | 4.38 | 3.10E+04 | 700 |
| ECS 585g | 5.4 | 1.20E+02 | 3.9 | 0.4 | 1.56 | 1.00E+07 | 290 | 5 | 0.5 | 2.5 | 6.40E+06 | 395 | 8.4 | 0.6 | 5.04 | 2.80E+04 | 700 |
| ECS 585i | 5.4 | 3.60E+03 | 4 | 0.4 | 1.6 | 9.40E+06 | 289 | 5 | 0.4 | 2 | 8.70E+06 | 400 | 7.8 | 0.6 | 4.68 | 7.40E+03 | 700 |
| ECS 585j | 5.3 | 7.90E+04 | 3.6 | 0.4 | 1.44 | 1.07E+07 | 285 | 5 | 0.4 | 2 | 4.20E+06 | 433 | 7.3 | 0.6 | 4.38 | 3.70E+04 | 690 |
| ECS 585l | 5.4 | 1.12E+07 | 4.3 | 0.4 | 1.72 | 8.80E+06 | 297 | 5 | 0.4 | 2 | 5.80E+06 | 360 | 7.9 | 0.6 | 4.74 | 1.60E+04 | 704 |
| SINK a | 5.6 | 4.60E+01 | 4.1 | 0.4 | 1.64 | 1.12E+07 | 300 | 5 | 0.5 | 2.5 | 9.00E+06 | 450 | 8 | 0.6 | 4.8 | 1.30E+05 | 705 |
| SINK c | 5.2 | 4.80E+01 | 3.7 | 0.4 | 1.48 | 1.04E+07 | 290 | 5 | 0.5 | 2.5 | 7.50E+06 | 480 | 7.1 | 0.6 | 4.26 | 3.60E+05 | 701 |
| C | 5.7 | 200 | 3.8 | 0.41 | 1.558 | 1.25E+03 | 291 | 5 | 0.46 | 2.3 | 880 | 444 | 7.6 | 0.5 | 3.8 | 19000 | 702 |

FIG. 11D

| ELEMENT | ROOM TEMP HEATER ohm | ROOM TEMP SENSOR ohm | AFTER CV | AFTER CI | AFTER WATTS | AFTER C ohm SENSOR | AFTER C TEMP | AFTER C CV | AFTER C CI | AFTER C WATTS | AFTER C ohm SENSOR | AFTER C TEMP | AFTER C CV | AFTER C CI | AFTER C WATTS | AFTER C ohm SENSOR | AFTER C TEMP |
|---|---|---|---|---|---|---|---|---|---|---|---|---|---|---|---|---|---|
| FN1 | 5.2 | 6.00E+06 | 4.3 | 0.4 | 1.72 | 5.50E+06 | 300 | 5 | 0.5 | 2.5 | 4.30E+06 | 357 | 8.2 | 0.6 | 4.92 | 1.10E+04 | 695 |
| FN2 | 5.5 | 5.50E+06 | 4.6 | 0.4 | 1.84 | 5.10E+06 | 300 | 5 | 0.5 | 2.5 | 5.00E+06 | 330 | 7.6 | 0.6 | 4.56 | 3.10E+04 | 710 |
| FN3 | 5.2 | 4.30E+06 | 3.7 | 0.4 | 1.48 | 4.10E+06 | 300 | 5 | 0.5 | 2.5 | 3.70E+06 | 400 | 7.3 | 0.6 | 4.38 | 2.75E+05 | 700 |
| FN6 | 5.5 | 3.10E+06 | 4.5 | 0.4 | 1.8 | 3.10E+06 | 285 | 5 | 0.4 | 2 | 2.90E+06 | 380 | 7.9 | 0.6 | 4.74 | 3.22E+05 | 700 |
| FN7 | 5.8 | 7.70E+06 | 4.3 | 0.4 | 1.72 | 7.60E+06 | 295 | 5 | 0.4 | 2 | 7.60E+06 | 380 | 8 | 0.6 | 4.8 | 6.40E+06 | 704 |
| FN8 | 5.6 | 4.10E+06 | 3.7 | 0.4 | 1.48 | 4.00E+06 | 300 | 5 | 0.5 | 2.5 | 3.90E+06 | 460 | 7 | 0.6 | 4.2 | 3.10E+06 | 700 |
| FN10 | 5.2 | 6.40E+06 | 4.4 | 0.4 | 1.76 | 6.20E+06 | 293 | 5 | 0.4 | 2 | 5.70E+06 | 430 | 7.5 | 0.6 | 4.5 | 9.00E+05 | 692 |
| ECS 869b | 5.9 | 6.50E+08 | 3.7 | 0.4 | 1.48 | 6.30E+08 | 300 | 5 | 0.4 | 2 | 5.80E+08 | 435 | 7.3 | 0.6 | 4.38 | 5.80E+05 | 703 |
| ECS 869d | 5.2 | 9.10E+06 | 3.8 | 0.4 | 1.52 | 8.90E+06 | 288 | 5 | 0.5 | 2.5 | 8.80E+06 | 445 | 7.2 | 0.6 | 4.32 | 6.90E+06 | 703 |
| IHSABb | 5.4 | 2.05E+07 | 3.6 | 0.4 | 1.44 | 2.00E+07 | 303 | 5 | 0.4 | 2 | 1.96E+07 | 465 | 7.3 | 0.6 | 4.38 | 1.58E+07 | 698 |
| IHSABd | 5.3 | 3.00E+06 | 4.3 | 0.4 | 1.72 | 2.80E+06 | 290 | 5 | 0.4 | 2 | 2.80E+06 | 365 | 8 | 0.6 | 4.8 | 2.40E+06 | 700 |
| IHSABf | 5.2 | 2.60E+06 | 4.8 | 0.4 | 1.92 | 2.50E+06 | 295 | 5 | 0.4 | 2 | 2.50E+06 | 333 | 8 | 0.6 | 4.8 | 1.90E+06 | 697 |
| IHSABg | 5.5 | 4.00E+06 | 3.9 | 0.4 | 1.56 | 3.80E+06 | 303 | 5 | 0.6 | 3 | 3.80E+06 | 370 | 8 | 0.6 | 4.8 | 2.00E+06 | 709 |
| ECS 585a | 5.1 | 3.40E+07 | 3.6 | 0.4 | 1.44 | 3.60E+07 | 310 | 5 | 0.5 | 2.5 | 3.30E+07 | 460 | 7.2 | 0.6 | 4.32 | 1.05E+07 | 701 |
| ECS 585e | 5.2 | 1.10E+08 | 3.4 | 0.4 | 1.36 | 1.10E+08 | 290 | 5 | 0.5 | 2.5 | 1.07E+08 | 500 | 6.9 | 0.6 | 4.14 | 6.10E+07 | 711 |
| FORMb | 5.3 | 1.30E+08 | 3.7 | 0.4 | 1.48 | 1.40E+07 | 290 | 5 | 0.5 | 2.5 | 1.80E+08 | 465 | 7.2 | 0.6 | 4.32 | 4.60E+04 | 712 |
| FORMc | 5.5 | 1.58E+07 | 4 | 0.4 | 1.6 | 9.60E+06 | 303 | 5 | 0.4 | 2 | 9.00E+06 | 321 | 7.7 | 0.6 | 4.62 | 1.35E+05 | 707 |

FIG. 7E

| | | | | | | | | | | | | | | | |
|---|---|---|---|---|---|---|---|---|---|---|---|---|---|---|---|
| FORMe | 5.3 | 1.70E+07 | 4.5 | 0.4 | 1.8 | 1.49E+07 | 290 | 5 | 0.5 | 2.5 | 3.30E+06 | 348 | 7.7 | 0.6 | 4.62 | 3.50E+05 | 695 |
| FORMf | 5.4 | 7.00E+06 | 3.7 | 0.4 | 1.48 | 6.30E+06 | 290 | 5 | 0.5 | 2.5 | 1.90E+06 | 355 | 7.8 | 0.6 | 4.68 | 1.15E+05 | 709 |
| FORMg | 5.3 | 6.30E+05 | 5 | 0.4 | 2 | 6.20E+05 | 285 | 5 | 0.4 | 2 | 6.20E+05 | 302 | 8.5 | 0.6 | 5.1 | 5.33E+05 | 690 |
| FORMh | 5.7 | 8.00E+05 | 4.8 | 0.4 | 1.92 | 1.20E+06 | 302 | 5 | 0.5 | 2.5 | 1.20E+06 | 320 | 8.3 | 0.6 | 4.98 | 8.95E+05 | 710 |
| FORMi | 5.5 | 5.70E+06 | 4.4 | 0.4 | 1.76 | 5.70E+06 | 311 | 5 | 0.5 | 2.5 | 5.70E+06 | 380 | 8.2 | 0.6 | 4.92 | 4.40E+06 | 704 |
| 1998CATa | 5.7 | 1.57E+01 | 4 | 0.4 | 1.6 | 4.50E+01 | 298 | 5 | 0.5 | 2.5 | 4.80E+01 | 403 | 8.5 | 0.6 | 5.1 | 5.20E+01 | 690 |
| 1998CATb | 5 | 3.05E+01 | 3.1 | 0.4 | 1.24 | 5.00E+01 | 306 | 5 | 0.4 | 2 | 6.10E+01 | 405 | 6.8 | 0.6 | 4.08 | 7.20E+01 | 714 |
| 1998CATc | 5.4 | 4.90E+05 | 4.6 | 0.4 | 1.84 | 4.80E+05 | 302 | 5 | 0.5 | 2.5 | 4.80E+05 | 319 | 8.3 | 0.6 | 4.98 | 4.75E+05 | 695 |
| 1998CATd | 5.4 | 1.78E+05 | 4.4 | 0.4 | 1.76 | 1.71E+05 | 290 | 5 | 0.4 | 2 | 1.72E+05 | 370 | 8.2 | 0.6 | 4.92 | 1.65E+05 | 704 |
| 1998CATe | 6 | 8.90E+06 | 4.1 | 0.4 | 1.64 | 8.80E+06 | 305 | 5 | 0.5 | 2.5 | 8.80E+06 | 353 | 7.8 | 0.6 | 4.68 | 5.60E+06 | 708 |
| 1998CATf | 5.4 | 2.00E+06 | 4 | 0.4 | 1.6 | 1.70E+06 | 297 | 5 | 0.4 | 2 | 1.60E+06 | 354 | 7.9 | 0.6 | 4.74 | 5.40E+01 | 708 |
| GENa | 5.5 | 5.80E+06 | 4 | 0.4 | 1.56 | 5.60E+06 | 295 | 5 | 0.5 | 2.5 | 5.60E+06 | 360 | 7.8 | 0.6 | 4.68 | 4.30E+06 | 715 |
| GENb | 5.7 | 6.20E+06 | 3.9 | 0.4 | 1.72 | 5.90E+06 | 300 | 5 | 0.4 | 2 | 5.90E+06 | 360 | 7.5 | 0.6 | 4.5 | 3.60E+06 | 706 |
| GENc | 6.2 | 4.30E+06 | 4.3 | 0.4 | 1.72 | 4.00E+06 | 310 | 5 | 0.5 | 2.5 | 4.00E+06 | 320 | 8 | 0.6 | 4.8 | 3.00E+06 | 715 |
| GENd | 5.8 | 4.80E+06 | 4.3 | 0.4 | 1.76 | 4.70E+06 | 294 | 5 | 0.5 | 2.5 | 4.60E+06 | 340 | 7.9 | 0.6 | 4.74 | 1.60E+06 | 711 |
| GENe | 5.8 | 1.87E+07 | 4.4 | 0.4 | 1.76 | 3.80E+03 | 300 | 5 | 0.4 | 2 | 3.70E+03 | 365 | 7.9 | 0.6 | 4.74 | 3.60E+03 | 695 |
| ECS 585g | 5.3 | 5.30E+01 | 3.1 | 0.4 | 1.24 | 8.00E+01 | 285 | 5 | 0.5 | 2.5 | 9.70E+01 | 500 | 6.5 | 0.6 | 3.9 | 1.10E+02 | 695 |
| ECS 585i | 5.7 | 1.40E+05 | 5 | 0.4 | 2 | 1.36E+05 | 290 | 5 | 0.5 | 2.5 | 1.36E+05 | 302 | 8.6 | 0.6 | 5.16 | 1.35E+05 | 704 |
| ECS 585j | 5.3 | 1.60E+05 | 4 | 0.4 | 1.6 | 1.57E+05 | 302 | 5 | 0.4 | 2 | 1.56E+05 | 402 | 8 | 0.6 | 4.8 | 1.47E+05 | 703 |
| SINKa | 5.5 | 7.90E+06 | 4.1 | 0.4 | 1.64 | 7.80E+06 | 290 | 5 | 0.5 | 2.5 | 7.60E+06 | 320 | 7.8 | 0.6 | 4.68 | 5.45E+05 | 705 |
| SINKc | 5.4 | 4.30E+06 | 3 | 0.4 | 1.2 | 4.20E+06 | 285 | 5 | 0.5 | 2.5 | 3.60E+06 | 530 | 6.5 | 0.6 | 3.9 | 4.50E+05 | 706 |
| IHSABi | 5.2 | 4.80E+05 | 3.9 | 0.4 | 1.56 | 4.75E+05 | 296 | 5 | 0.5 | 2.5 | 4.76E+05 | 440 | 7.8 | 0.6 | 4.68 | 4.65E+05 | 711 |
| IHSABj | 5.2 | 1.85E+01 | 3.6 | 0.4 | 1.44 | 2.60E+01 | 295 | 5 | 0.5 | 2.5 | 2.90E+01 | 455 | 7.1 | 0.6 | 4.26 | 3.20E+01 | 703 |
| IHSABk | 5.2 | 3.00E+01 | 3.7 | 0.4 | 1.48 | 4.00E+01 | 294 | 5 | 0.5 | 2.5 | 4.40E+01 | 450 | 7.3 | 0.6 | 4.38 | 5.00E+01 | 704 |
| IHSABm | 5.3 | 4.10E+01 | 4.3 | 0.4 | 1.72 | 1.75E+02 | 290 | 5 | 0.5 | 2.5 | 1.59E+02 | 370 | 7.9 | 0.6 | 4.74 | 1.63E+02 | 695 |
| IHSABn | 5.3 | 6.70E+06 | 4.1 | 0.4 | 1.64 | 6.80E+06 | 292 | 5 | 0.5 | 2.5 | 6.60E+06 | 333 | 7.7 | 0.6 | 4.62 | 1.50E+06 | 692 |

FIG. 11F

SYSTEM AND METHOD OF SENSOR RECONDITIONING IN AN EXHAUST AFTERTREATMENT SYSTEM

CROSS REFERENCE TO RELATED APPLICATIONS

This application is a National Stage of PCT Application No. PCT/US2015/058843, filed Nov. 3, 2015, which claims the benefit of priority to U.S. Provisional Patent Application No. 62/075,060, filed Nov. 4, 2014. The contents of both applications are incorporated herein by reference in their entireties.

TECHNICAL FIELD

The present disclosure relates to engine exhaust aftertreatment systems.

BACKGROUND

Emissions regulations for internal combustion engines have become more stringent over recent years. Environmental concerns have motivated the implementation of stricter emission requirements for internal combustion engines throughout much of the world. Governmental agencies, such as the Environmental Protection Agency (EPA) in the United States, carefully monitor the emission quality of engines and set emission standards to which engines must comply. Consequently, the use of exhaust aftertreatment systems on engines to reduce emissions is increasing.

Exhaust aftertreatment systems are generally designed to reduce emission of particulate matter, nitrogen oxides (NOx), hydrocarbons, and other environmentally harmful pollutants. However, the components that make up the exhaust aftertreatment system can be susceptible to failure and degradation. Because the failure or degradation of components may have adverse consequences on performance and the emission-reduction capability of the exhaust aftertreatment system, the detection and, if possible, correction of failed or degraded components is desirable. In fact, some regulations require on-board diagnostic (OBD) monitoring or testing of many of the components of the exhaust aftertreatment system.

SUMMARY

One embodiment relates to a system. The system includes an engine; an exhaust aftertreatment system in exhaust gas receiving communication with the engine, wherein the exhaust aftertreatment system includes a particulate matter sensor that includes a heating element structured to selectively provide heat to the particulate matter sensor; and a controller communicably coupled to the engine and the exhaust aftertreatment system. The controller is structured to: receive particulate matter data indicating a state of the particulate matter sensor; determine that the particulate matter sensor is in a full state based on the particulate matter data; and activate the heating element a number of times at intermittent temperatures prior to a final temperature. According to one embodiment, the final temperature refers to a temperature of the sensor that is high enough to fully clear the sensor, wherein a determination of fully clear is based on a measured resistance across the sensor being at or above a nominal resistance threshold. According to another embodiment, the number of intermittent temperatures includes activating the heating element of the particulate matter sensor to a first temperature range for a first duration; activating the heating element to a second temperature range for a second duration following the first duration; and activating the heating element to a third temperature range for a third duration following the second duration. According to one embodiment, the particulate matter sensor is structured as an interdigitated electrode sensor. In certain embodiments, the first temperature range is less than the second temperature range, which is less than the third temperature range. In still further embodiments, the delineations of each temperature range are based on one or more exhaust gas constituents, and potential poisons. Accordingly, the heating element is structured to burn-off specific exhaust gas constituents in a step-up fashion to substantially avoid combustion of many of the constituents at one time. This type of reaction reduces the reactivity of the combustion to substantially reduce a likelihood of damage to the sensor.

According to another embodiment, the controller is structured to evaluate the time substantially required to achieve the full state for the sensor and decide if the health state of a particulate filter in the aftertreatment system is good or bad. For example, if the time to achieve the full state occurs in less than X seconds, the controller may determine that the particulate filter is in a degraded or bad state.

Another embodiment relates to a method for reconditioning a particulate matter sensor in an exhaust aftertreatment system. The method includes receiving particulate matter data indicating a state of the particulate matter sensor; determining that the particulate matter sensor is in a full state based on the particulate matter data; activating a heating element of the particulate matter sensor to a first temperature range for a first duration; activating the heating element to a second temperature range for a second duration following the first duration; and activating the heating element to a third temperature range for a third duration following the second duration.

Still another embodiment relates to an apparatus for reconditioning a particulate matter sensor in an exhaust aftertreatment system. The apparatus includes a particulate matter (PM) sensor module structured to receive particulate matter data and determine that a particulate matter sensor of an exhaust aftertreatment system is in a full state based on the particulate matter data; and a heating element module communicably coupled to the PM sensor module, wherein the heating element module is structured to activate a heating element of the particulate matter sensor a number of times at intermittent temperatures prior to a final temperature.

These and other features, together with the organization and manner of operation thereof, will become apparent from the following detailed description when taken in conjunction with the accompanying drawings.

BRIEF DESCRIPTION OF THE DRAWINGS

FIGS. 5A-5B are spreadsheets of an experimental setup for testing an interdigitated particulate matter electrode sensor, according to an example embodiment.

Figure 6B:
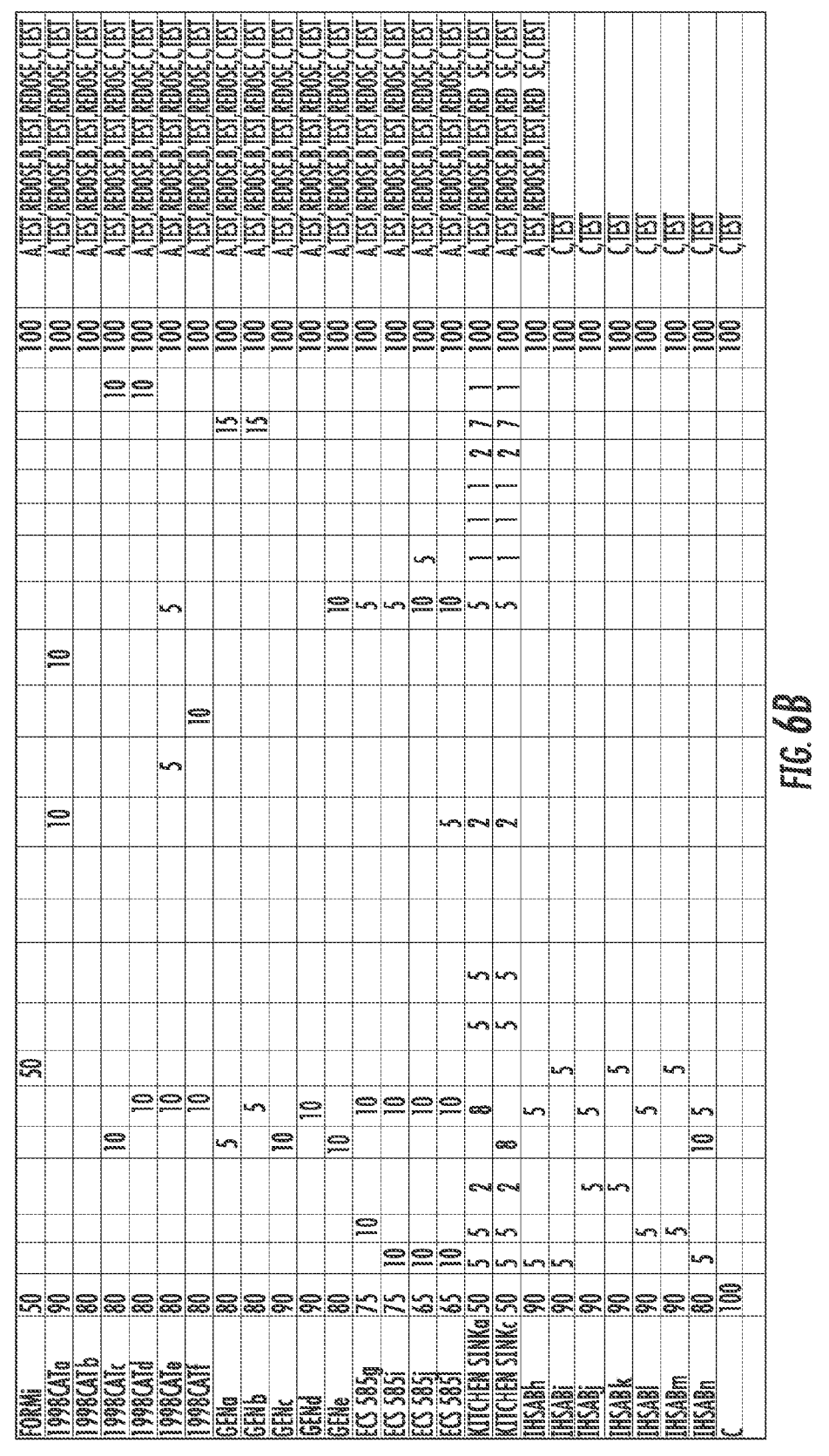
Figure 6D:
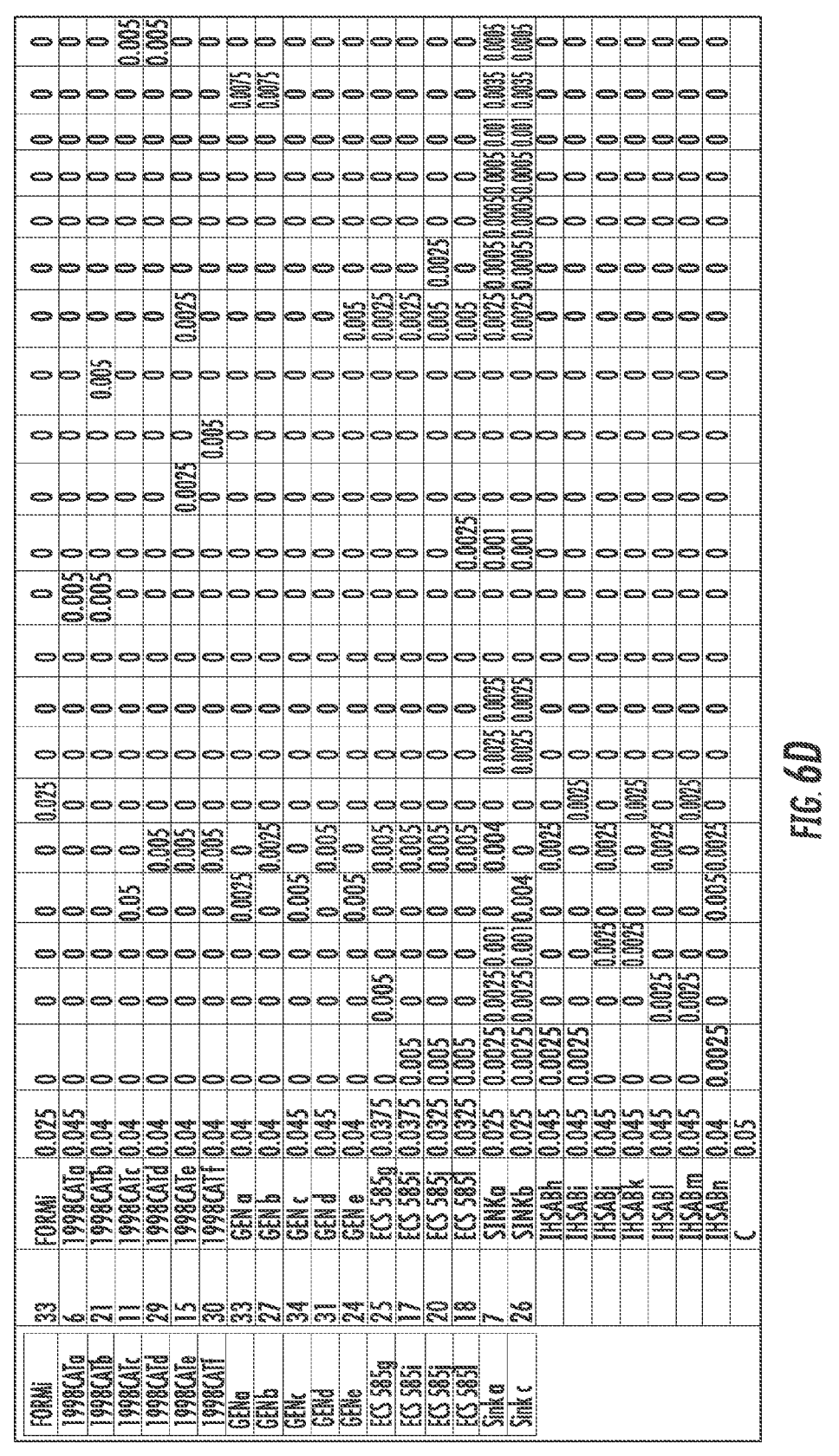

FIGS. 6A-6D are spreadsheets of a list of experiments run on the interdigitated particulate matter electrode sensor using the experimental setup of FIGS. 5A-5B.

Figure 7E:
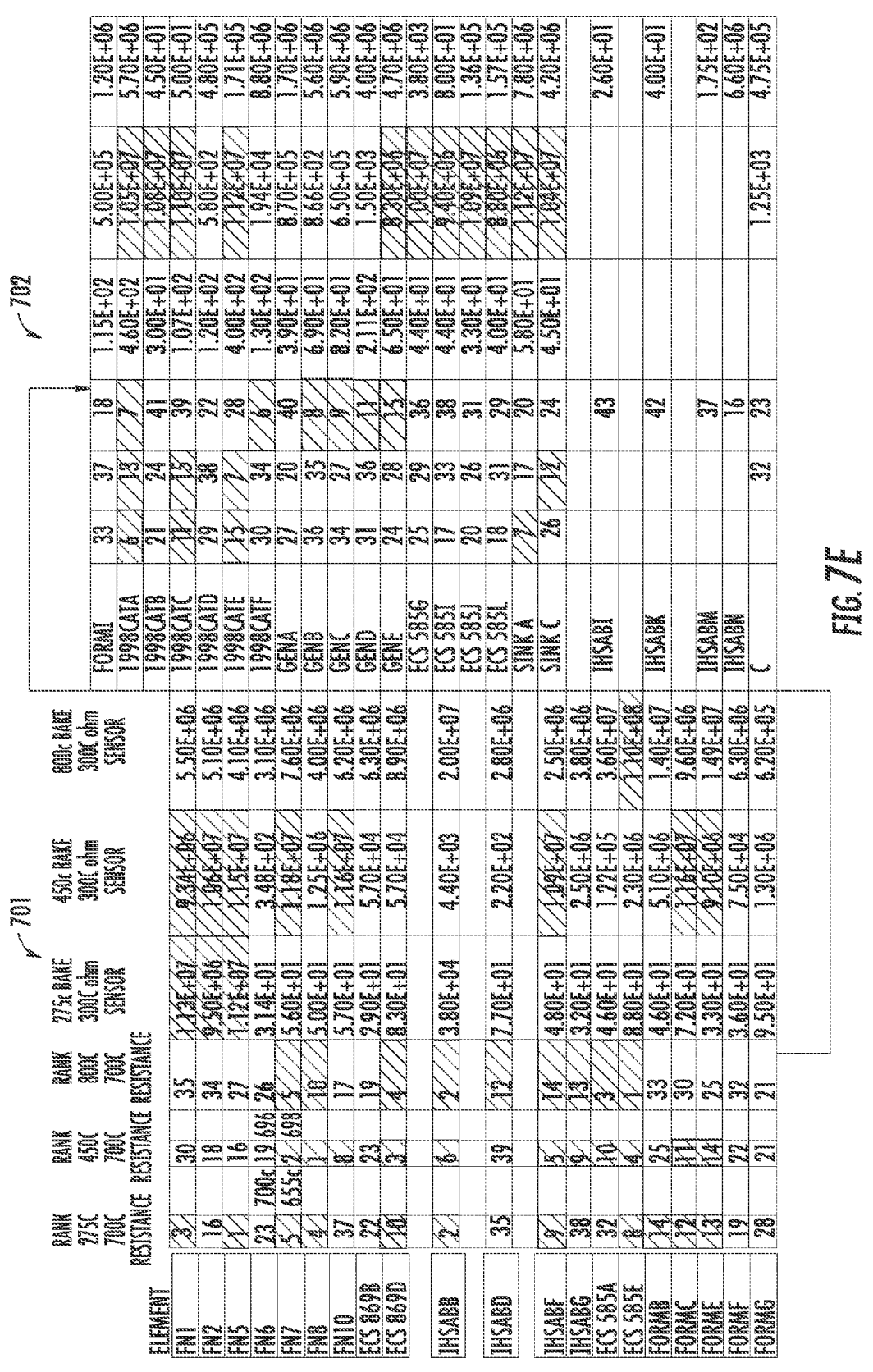

FIGS. 7A-7E depict the results of the experiments of FIGS. 6A-6D based on the setup of FIGS. 5A-5B, according to an example embodiment.

Figure 8A:
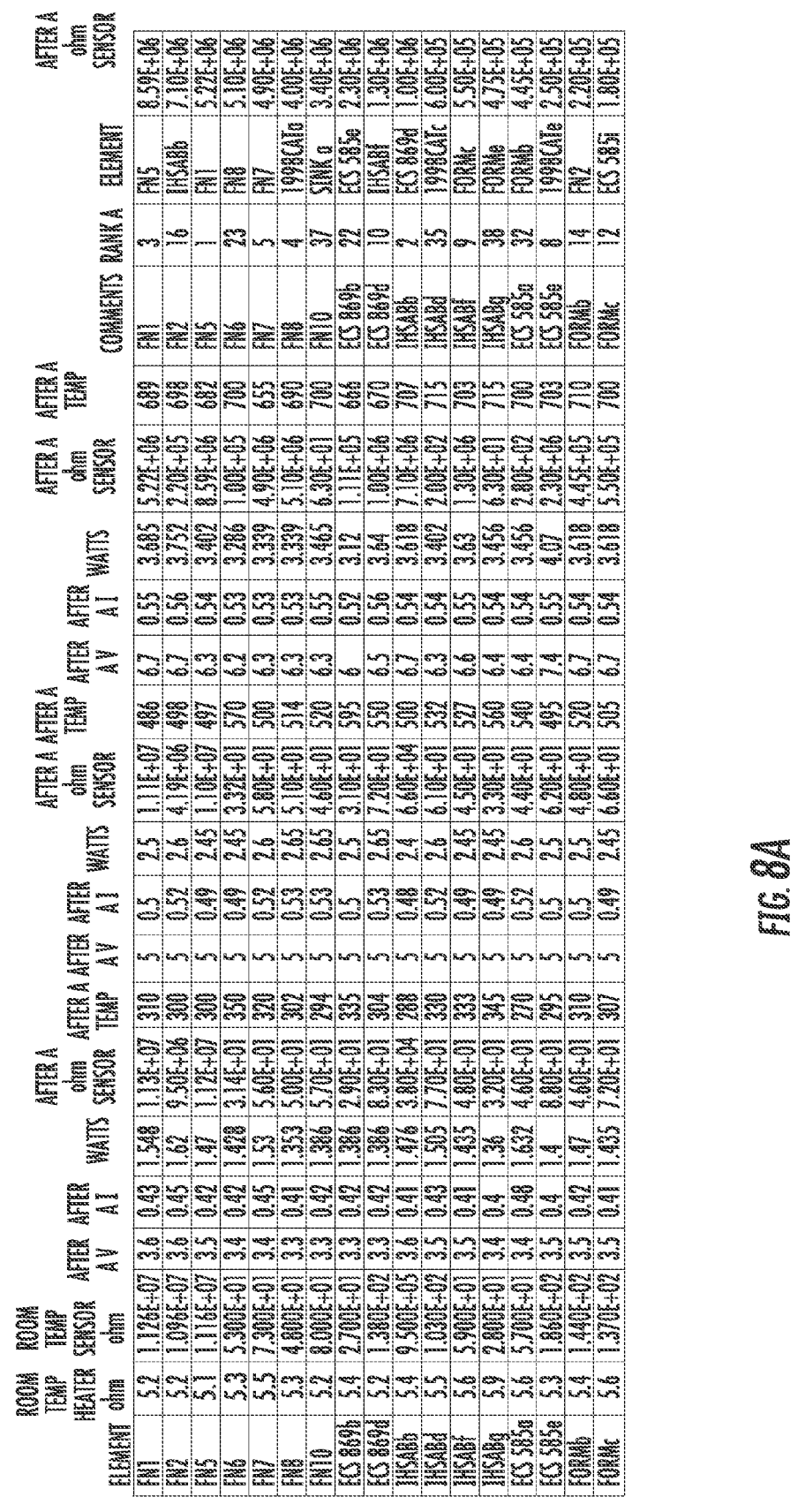
Figure 8B:
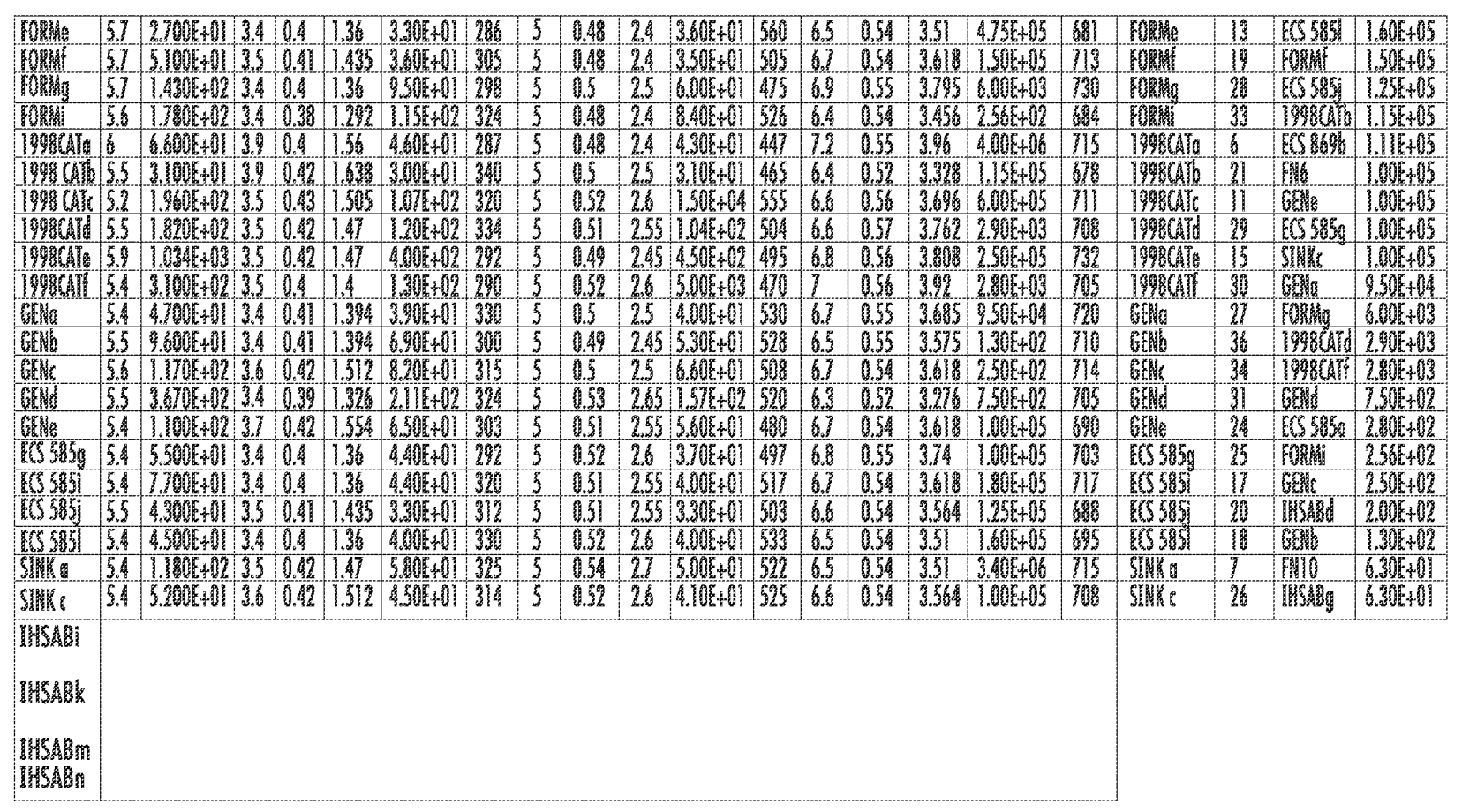

FIGS. 8A-8B depict the results of baking protocol "A" of FIGS. 5A-5B, according to an example embodiment.

Figure 9B:
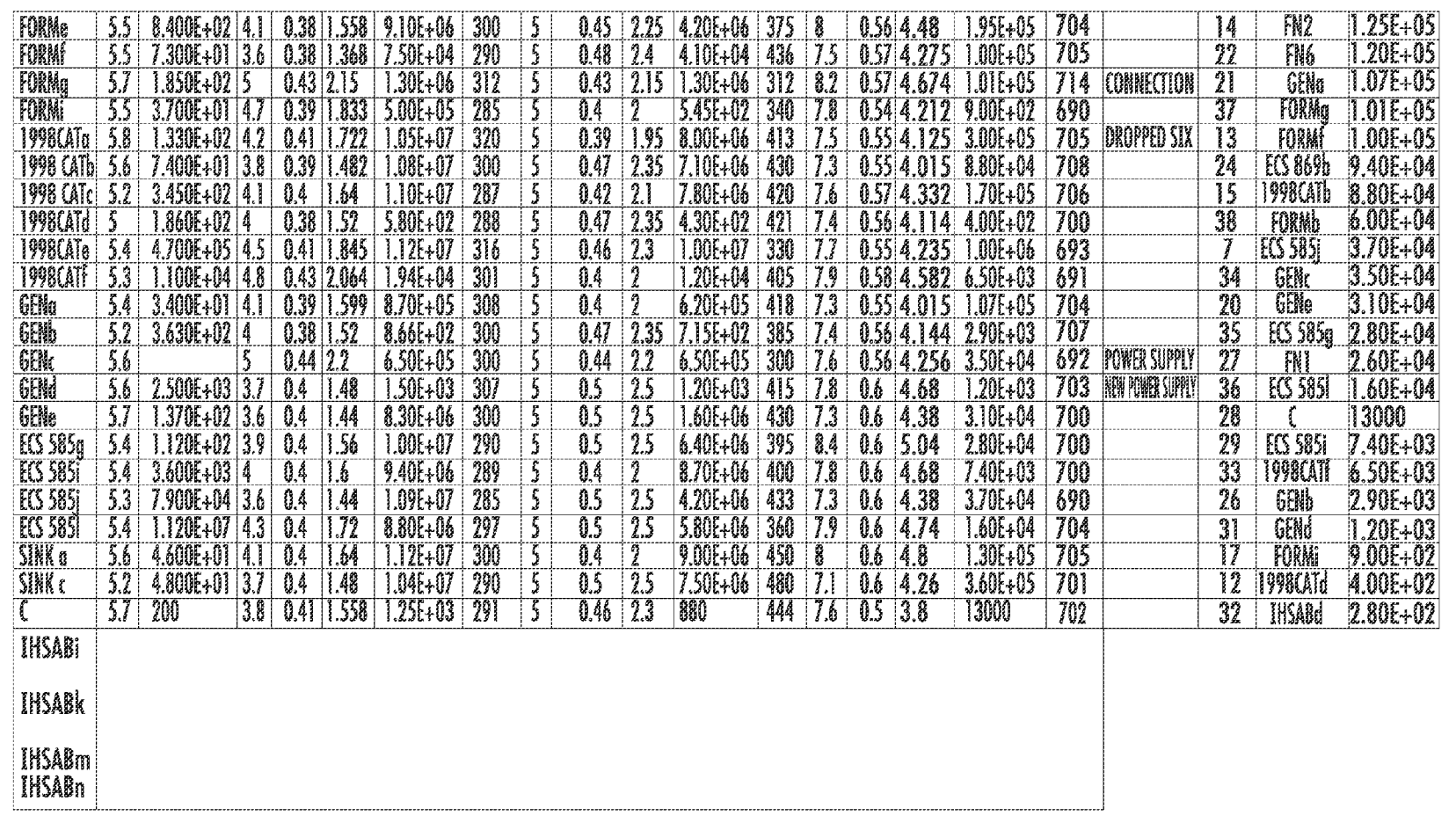

FIGS. 9A-9C depict the results of baking protocol "B" of FIGS. 5A-5B, according to an example embodiment.

Figure 10B:
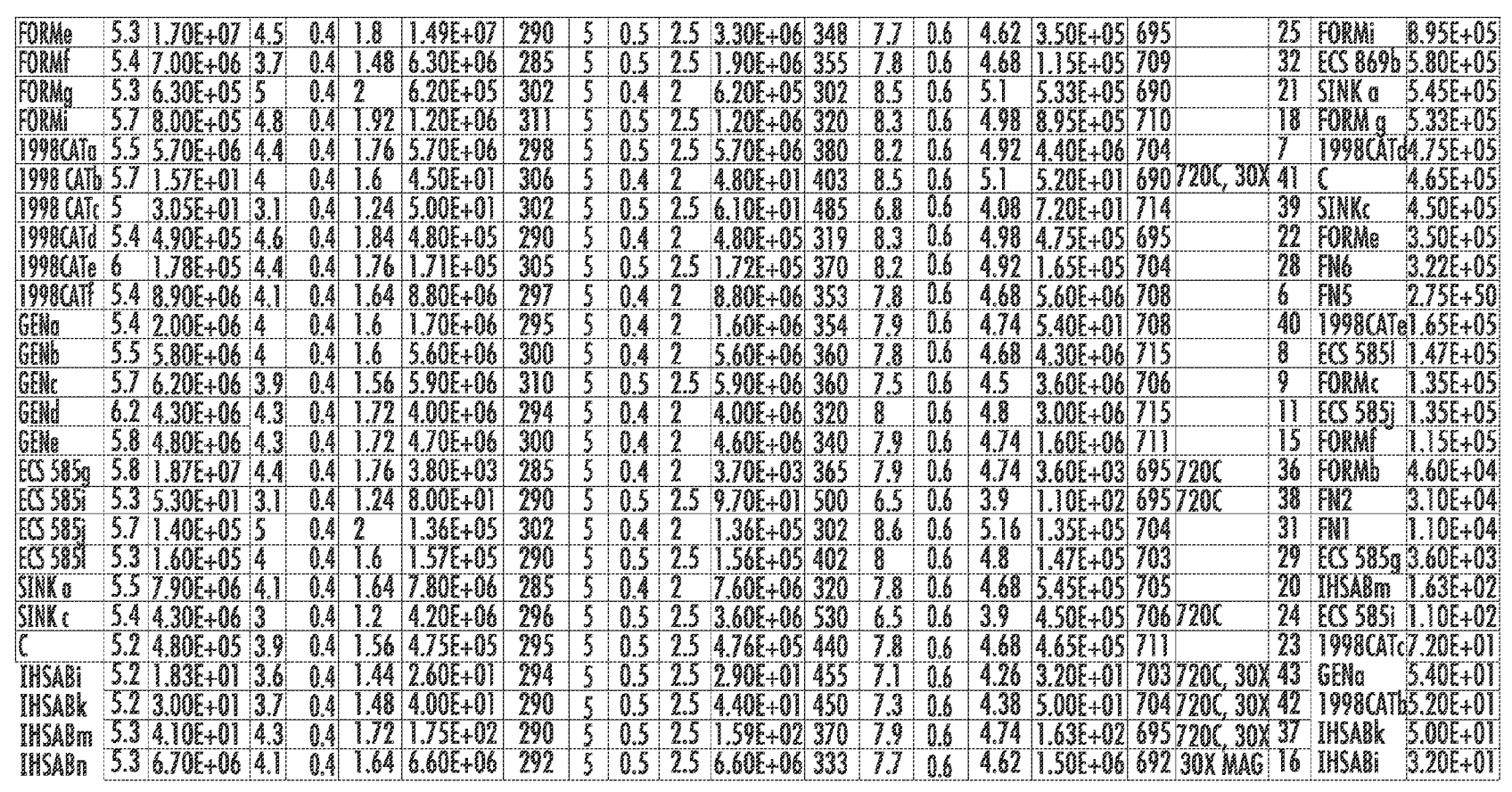

FIGS. 10A-10C depict the results of baking protocol "C" of FIGS. 5A-5B, according to an example embodiment.

FIGS. 11A-11F depict the results of FIGS. 8A-10C combined in one graph, according to an example embodiment.

DETAILED DESCRIPTION

Figure 1:
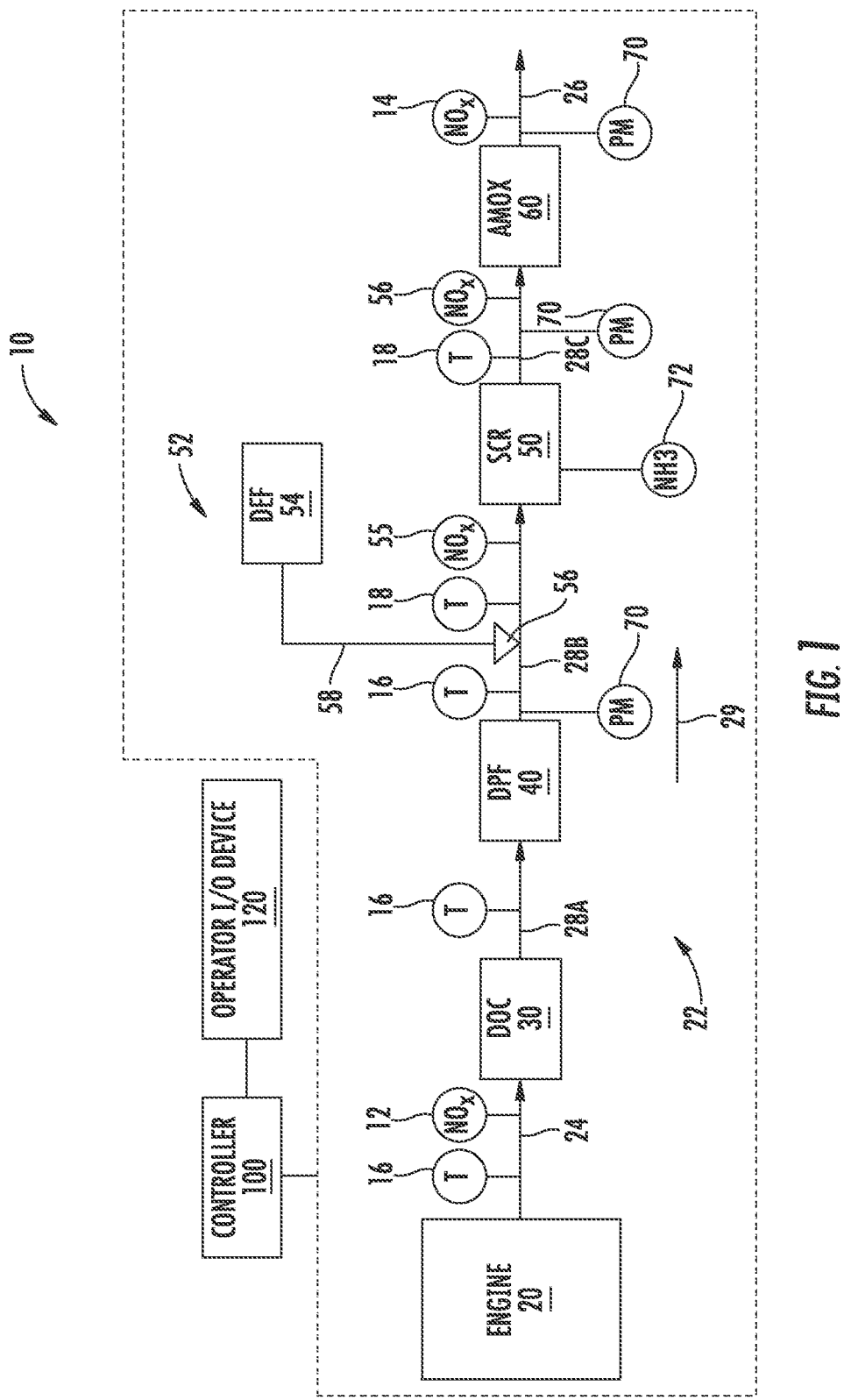
FIG. 1 is a schematic diagram of an exhaust aftertreatment system with a controller, according to an example embodiment.

Referring to the Figures generally, the various embodiments disclosed herein relate to a system and method of reconditioning a particulate matter (PM) sensor in an exhaust aftertreatment system. As described more fully herein, many exhaust aftertreatment systems include a diesel particulate filter (DPF). The DPF is structured to remove or substantially remove particulate matter (e.g., soot, ash, carbon and hydrocarbon compounds) in an exhaust gas stream. Over time, the DPF may become damaged and/or any other condition that hampers its ability to reduce particulate matter emissions from the engine. As a result, a relatively greater amount of particulate matter passes through the downstream exhaust aftertreatment components and is, consequently, emitted into the atmosphere. Not only is this emission potentially harmful to the atmosphere, but the particulate matter may become disruptive to the functionality of the other components, which also may cause an addition of harmful emissions (e.g., NOx). Accordingly, many exhaust aftertreatment systems include a PM sensor that monitors an amount of particulate matter traveling through the system. If the particulate matter is at or above a predetermined threshold, an indicator is activated requiring a service event to check on the health of the DPF. In some worst case situations, regulations require the engine to enter a reduced power mode until service is performed. However, over time, the PM sensor may accumulate poisoning that causes it to falsely determine the actual particulate matter emissions level.

According to the present disclosure, a PM sensor includes a heating element structured to provide heat to the PM sensor to burn off the accumulated particulate matter to recondition the sensor to restore its functionality. More particularly, the PM sensor is structured as an interdigitated or repetitive pattern sensor to which conductive soot or emissions are drawn (often with assistance of electrophoresis) over time. When the resistance between electrodes has dropped low enough, the time is noted from the last clean condition to the full condition and a judgment is made about the health of the particulate filter (as determined by a transfer function of soot rate to fill up time). Rather than simply providing an elevated temperature of heat for a preset amount of time, a controller provides one or more commands to the heating element to cause it heat the PM sensor in a stepped manner (e.g., 200 degrees Celsius for ten seconds, then 300-500 degrees Celsius for ten seconds, followed by at or above 700 degrees Celsius for fifteen seconds). Due to the exhaust gas flowing through an aftertreatment system containing many different constituents (e.g., ammonia (from diesel exhaust fluid), carbon, melamine, sulfur, biuret, soot and ash, etc.), each of these constituents tend to have different burn-off temperatures (e.g., the temperature at which the constituent is burned off, decomposed, and/or dislodged from a component in order for it to pass through the remainder of the system). Thus, by commanding the heating element to operate in a specific stepped-up manner to burn-off one or a few constituents at a time (described more fully herein), the problems associated with uncontrolled combustion may be avoided, which may prolong the life the PM sensor and reduce costs to the operator of the aftertreatment system (e.g., replacement and service costs). These and other features are described more fully herein.

Referring to FIG. 1, an engine exhaust aftertreatment system with a controller is shown, according to an example embodiment. The engine system 10 includes an internal combustion engine 20 and an exhaust aftertreatment system 22 in exhaust gas-receiving communication with the engine 20. According to one embodiment, the engine 20 is structured as a compression-ignition internal combustion engine that utilizes diesel fuel. However, in various alternate embodiments, the engine 20 may be structured as any other type of engine (e.g., spark-ignition) that utilizes any type of fuel (e.g., gasoline) or a power plant. Within the internal combustion engine 20, air from the atmosphere is combined with fuel, and combusted, to power the engine. Combustion of the fuel and air in the compression chambers of the engine 20 produces exhaust gas that is operatively vented to an exhaust manifold and to the exhaust aftertreatment system 22.

In the example depicted, the exhaust aftertreatment system 22 includes a diesel particular filter (DPF) 40, a diesel oxidation catalyst (DOC) 30, a selective catalytic reduction (SCR) system 52 with a SCR catalyst 50, and an ammonia oxidation (AMOX) catalyst 60. The SCR system 52 further includes a reductant delivery system that has a diesel exhaust fluid (DEF, a urea solution) source 54 that supplies DEF to a DEF doser 56 via a DEF line 58.

In an exhaust flow direction, as indicated by directional arrow 29, exhaust gas flows from the engine 20 into inlet piping 24 of the exhaust aftertreatment system 22. From the inlet piping 24, the exhaust gas flows into the DOC 30 and exits the DOC into a first section of exhaust piping 28A. From the first section of exhaust piping 28A, the exhaust gas flows into the DPF 40 and exits the DPF into a second section of exhaust piping 28B. From the second section of exhaust piping 28B, the exhaust gas flows into the SCR catalyst 50 and exits the SCR catalyst into the third section of exhaust piping 28C. As the exhaust gas flows through the second section of exhaust piping 28B, it is periodically dosed with DEF by the DEF doser 56. Accordingly, the second section of exhaust piping 28B acts as a decomposition chamber or tube to facilitate the decomposition of the DEF to ammonia. From the third section of exhaust piping 28C, the exhaust gas flows into the AMOX catalyst 60 and exits the AMOX catalyst into outlet piping 26 before the exhaust gas is expelled from the exhaust aftertreatment system 22. Based on the foregoing, in the illustrated embodiment, the DOC 30 is positioned upstream of the DPF 40 and the SCR catalyst 50, and the SCR catalyst 50 is positioned downstream of the DPF 40 and upstream of the AMOX catalyst 60. However, in alternative embodiments, other arrangements of the components of the exhaust aftertreatment system 22 are also possible. For example, in some embodiments, the AMOX catalyst 60 may be excluded from the system. In other embodiments, the AMOX catalyst 60 may be included with the SCR catalyst 50 (e.g., no exhaust gas piping section 28C). All such exhaust aftertreatment system configurations are intended to fall within the spirit and scope of the present disclosure.

The DOC 30 may have any of various flow-through designs. Generally, the DOC 30 is structured to oxidize at least some particulate matter, e.g., the soluble organic fraction of soot, in the exhaust and reduce unburned hydrocarbons and CO in the exhaust to less environmentally harmful compounds. For example, the DOC 30 may be structured to reduce the hydrocarbon and CO concentrations in the exhaust to meet the requisite emissions standards for those components of the exhaust gas. An indirect consequence of the oxidation capabilities of the DOC 30 is the ability of the DOC to oxidize NO into $NO_2$. In this manner, the level of $NO_2$ exiting the DOC 30 is equal to the $NO_2$ in the exhaust gas generated by the engine 20 plus the $NO_2$ converted from NO by the DOC.

In addition to treating the hydrocarbon and CO concentrations in the exhaust gas, the DOC 30 may also be used in the controlled regeneration of the DPF 40, SCR catalyst 50, and AMOX catalyst 60. This can be accomplished through the injection, or dosing, of unburned HC into the exhaust gas upstream of the DOC 30. Upon contact with the DOC 30, the unburned HC undergoes an exothermic oxidation reaction which leads to an increase in the temperature of the exhaust gas exiting the DOC 30 and subsequently entering the DPF 40, SCR catalyst 50, and/or the AMOX catalyst 60. The amount of unburned HC added to the exhaust gas is selected to achieve the desired temperature increase or target controlled regeneration temperature.

The DPF 40 may be any of various flow-through designs, and is structured to reduce particulate matter concentrations, e.g., soot and ash, in the exhaust gas to meet or substantially meet requisite emission standards. The DPF 40 captures particulate matter and other constituents, and thus may need to be periodically regenerated to burn off the captured constituents. Additionally, the DPF 40 may be configured to oxidize NO to form $NO_2$ independent of the DOC 30.

As discussed above, the SCR system 52 may include a reductant delivery system with a reductant (e.g., DEF) source 54, a pump and a delivery mechanism or doser 56. The reductant source 54 can be a container or tank capable of retaining a reductant, such as, for example, ammonia ($NH_3$), DEF (e.g., urea), or diesel oil. The reductant source 54 is in reductant supplying communication with the pump, which is configured to pump reductant from the reductant source to the delivery mechanism 56 via a reductant delivery line 58. The delivery mechanism 56 is positioned upstream of the SCR catalyst 50. The delivery mechanism 56 is selectively controllable to inject reductant directly into the exhaust gas stream prior to entering the SCR catalyst 50. As described herein, the controller 100 is structured to control the timing and amount of the reductant delivered to the exhaust gas. In some embodiments, the reductant may either be ammonia or DEF, which decomposes to produce ammonia. As briefly described above, the ammonia reacts with NOx in the presence of the SCR catalyst 50 to reduce the NOx to less harmful emissions, such as $N_2$ and $H_2O$. The NOx in the exhaust gas stream includes $NO_2$ and NO. Generally, both $NO_2$ and NO are reduced to $N_2$ and $H_2O$ through various chemical reactions driven by the catalytic elements of the SCR catalyst in the presence of $NH_3$.

The SCR catalyst 50 may be any of various catalysts known in the art. For example, in some implementations, the SCR catalyst 50 is a vanadium-based catalyst, and in other implementations, the SCR catalyst is a zeolite-based catalyst, such as a Cu-Zeolite or a Fe-Zeolite catalyst.

The AMOX catalyst 60 may be any of various flow-through catalysts configured to react with ammonia to produce mainly nitrogen. As briefly described above, the AMOX catalyst 60 is structured to remove ammonia that has slipped through or exited the SCR catalyst 50 without reacting with NOx in the exhaust. In certain instances, the exhaust aftertreatment system 22 may be operable with or without an AMOX catalyst. Further, although the AMOX catalyst 60 is shown as a separate unit from the SCR catalyst 50 in FIG. 1, in some implementations, the AMOX catalyst may be integrated with the SCR catalyst, e.g., the AMOX catalyst and the SCR catalyst can be located within the same housing. According to the present disclosure, the SCR catalyst and AMOX catalyst are positioned serially, with the SCR catalyst preceding the AMOX catalyst. As described above, in various other embodiments, the AMOX catalyst is not included in the exhaust aftertreatment system 22. In these embodiments, the NOx sensor 14 may be excluded from the exhaust aftertreatment system 22 as well.

Various sensors, such as $NH_3$ sensor 72, NOx sensors 12, 14, 55, 57 and temperature sensors 16, 18, may be strategically disposed throughout the exhaust aftertreatment system 22 and may be in communication with the controller 100 to monitor operating conditions of the engine system 10. As shown, more than one NOx sensor may be positioned upstream and downstream of the SCR catalyst 50. In this configuration, the NOx sensor 12 measures the engine out NOx while the NOx sensor 55 measures the SCR catalyst 50 inlet NOx amount, which is referred to as the SCR inlet NOx sensor 55 herein. Due to the DOC 30/DPF 40 potentially oxidizing some portion of the engine out NOx, the engine out NOx amount may not be equal to the SCR catalyst 50 inlet NOx amount. Accordingly, this configuration accounts for this potential discrepancy. The NOx amount leaving the SCR catalyst 50 may be measured by the NOx sensor 57 and/or the NOx sensor 14. In some embodiments, there may be only NOx sensor 57 or NOx sensor 14 depending on whether the configuration of the exhaust aftertreatment system 22 includes the AMOX catalyst 60. The NOx sensor 57 is positioned downstream of the SCR catalyst 50 and is structured to detect the concentration of NOx in the exhaust gas downstream of the SCR catalyst 50 (e.g., exiting the SCR catalyst), which is referred to as the SCR outlet NOx sensor 57 herein.

The temperature sensors 16 are associated with the DOC 30 and DPF 40, and thus can be defined as the DOC/DPF temperature sensors 16. The DOC/DPF temperature sensors are strategically positioned to detect the temperature of exhaust gas flowing into the DOC 30, out of the DOC and into the DPF 40, and out of the DPF before being dosed with DEF by the doser 56. The temperature sensors 18 are associated with the SCR catalyst 50 and thus can be defined as SCR temperature sensors 18. The SCR temperature sensors 18 are strategically positioned to detect the temperature of exhaust gas flowing into and out of the SCR catalyst 50.

Although the exhaust aftertreatment system 22 shown includes one of a DOC 30, DPF 40, SCR catalyst 50, and AMOX catalyst 60 positioned in specific locations relative to each other along the exhaust flow path, in other embodiments, the exhaust aftertreatment system may include more than one of any of the various catalysts positioned in any of various positions relative to each other along the exhaust flow path as desired. Further, although the DOC 30 and AMOX catalyst 60 are non-selective catalysts, in some embodiments, the DOC and AMOX catalyst can be selective catalysts.

FIG. 1 is also shown to include an operator input/output (I/O) device 120. The operator I/O device 120 is communicably coupled to the controller 100, such that information may be exchanged between the controller 100 and the I/O device 120, wherein the information may relate to one or more components of FIG. 1 or determinations (described below) of the controller 100. The operator I/O device 120 enables an operator of the engine system 10 to communicate with the controller 100 and one or more components of the engine system 10 of FIG. 1. For example, the operator input/output device 120 may include, but is not limited to, an interactive display, a touchscreen device, a diagnostic tool separate from the engine-exhaust aftertreatment system, one or more buttons and switches, voice command receivers, etc. In various alternate embodiments, the controller 100 and components described herein may be implemented with non-vehicular applications (e.g., a power generator). Accordingly, the I/O device may be specific to those applications. For example, in those instances, the I/O device may include a laptop computer, a tablet computer, a desktop computer, a phone, a watch, a personal digital assistant, etc. Via the I/O device 120, the controller 100 may provide a fault or service notification based on the determined state of one or more components of the aftertreatment system.

As shown in FIG. 1, a particulate matter (PM) sensor 70 is positioned downstream of the SCR 50. According to one embodiment, the PM sensor 70 is positioned in any position downstream of the DPF 40. Accordingly, other locations of the PM sensor 70 are also depicted in FIG. 1: after the DPF 40, after the AMOX catalyst 60, etc. In some embodiments, more than one PM sensor 70, as shown in FIG. 1, may also be included in the system. The PM sensor 70 is structured to monitor particulate matter flowing through the exhaust aftertreatment system. By monitoring the particulate matter, the PM sensor 70 monitors the functionality of the DPF 40. If an amount of particulate matter is sensed above a threshold, the PM sensor 70 may determine low functionality of the DPF 40 and provide a notification to an operator via I/O device 120.

Figure 2:
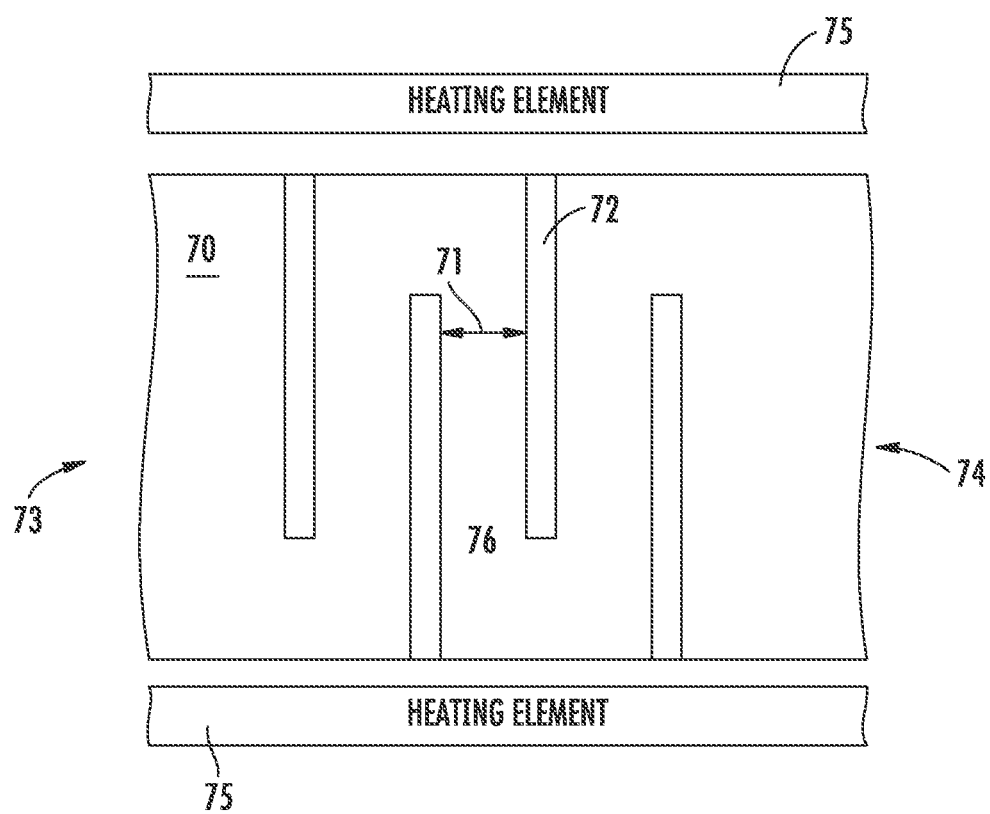
FIG. 2 is a schematic diagram of an exemplary particulate matter sensor used in the exhaust aftertreatment system of FIG. 1.
Figure 14:
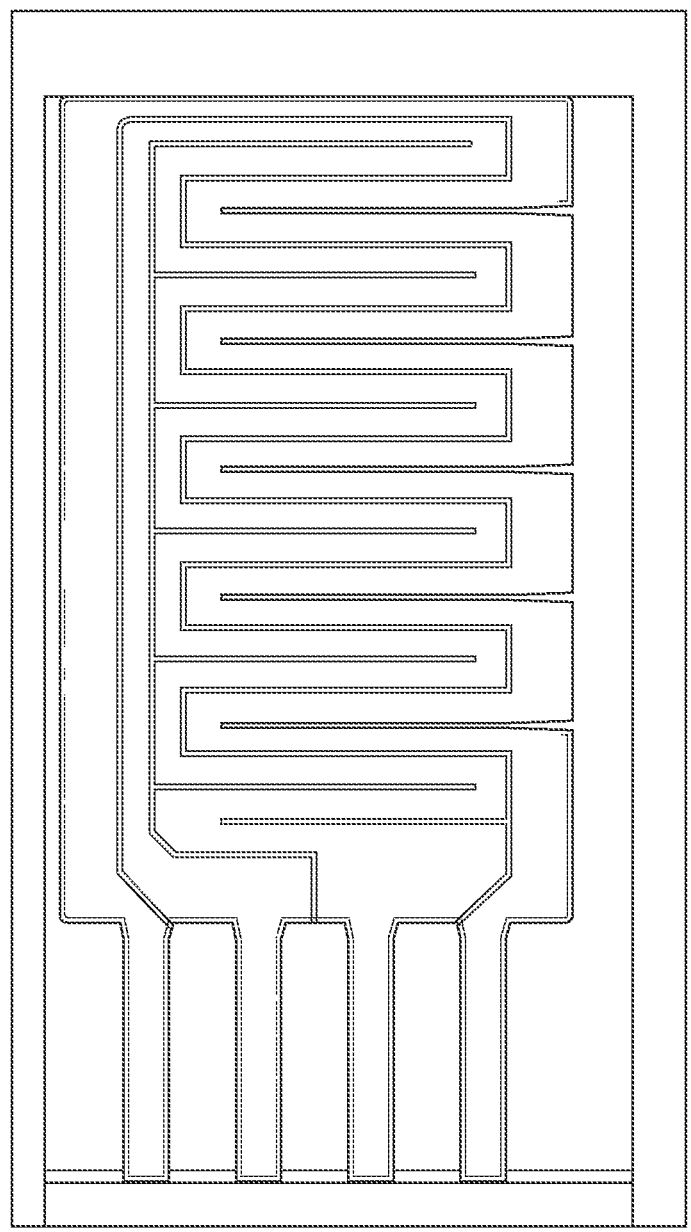
FIG. 14 depicts schematic diagram of an actual interdigitated electrode sensor, according to an example embodiment.

Referring to FIG. 2, a schematic diagram of an exemplary PM sensor 70 used in the aftertreatment system of FIG. 1 is shown. An actual schematic illustration of an interdigitated electrode sensor is shown in FIG. 14. In the example shown, the PM sensor 70 is structured as an interdigitated PM electrode sensor with digits 72 that define a gap 71 between the digits 72 (e.g., traces). To monitor a soot or particulate matter emission rate, a resistance is measured across the PM sensor 70 (e.g., between inlet end 73 and outlet end 74). For this purpose, either the field encompassing the gap 71 is an electrical insulator and the traces 72 are electrical conductors, or the traces 72 are insulators and the gaps 71 are conductors. The measured resistance is transmitted to the controller 100, where the controller 100 determines whether the particulate matter emission is within (or not within) an acceptable emissions rate based on the measured resistance (e.g., whether the measured resistance is at or below a resistance threshold). In some other embodiments, the determination includes a time-based element. For example, the controller 100 evaluates the duration it takes for the PM sensor 70 to go from an empty or clear state (indicated by a resistance value greater than or equal to a nominal resistance threshold for the sensor, which is caused by a relatively low amount of conductive constituents in the gap 71) to a full state (indicated by a resistance value less than or a nominal resistance threshold for the sensor, which is caused by a relatively high amount of conductive exhaust gas constituents in the gap 71). If the empty-to-full state transition occurs in a less than or equal amount of time threshold (e.g., twenty seconds), the controller 100 may determine that the DPF needs to be examined. The controller 100 may also determine that reconditioning of the PM sensor 70, as described in greater detail below, should be performed.

If sensor recondition is commanded, the controller 100 reacts by activating the heating element 75 to burn off the accumulated exhaust gas constituents. In operation, over time, conductive constituents in the exhaust gas stream (e.g., carbon) accumulate within the gap 71. The accumulation of conductive constituents lowers the resistance across the PM sensor 70. Accordingly, even if the DPF 40 is functioning correctly, the accumulation of the constituents may cause a faulty measurement of the particulate matter emissions rate by the PM sensor 70, which may lead to unnecessary technician service visits to remedy the DPF 40. Accordingly, as described more fully below, the PM sensor 70 is periodically heated to burn off the accumulated exhaust gas constituents to restore functionality of the PM sensor 70.

According to various other embodiments, the PM sensor 70 may be structured as any type (or group of PM sensors) that are structured to monitor the particulate matter emissions rate in an exhaust aftertreatment system. For example, other PM sensor types may include a flowrate monitor (e.g., At a certain engine speed and torque, the expected flowrate (e.g., via computer simulation, via a lookup table the speed and torque, etc.) of the exhaust is X unit mass/unit time. If the measured flowrate of the exhaust gas is below this expected value, the controller may determine a fault condition exists with the DPF 40). All such variations are intended to fall within the spirit and scope of the present disclosure.

As mentioned above, the PM sensor 70 includes a heating element 75. In the example of FIG. 2, the heating element 75 is structured as a resistance-type heating element (e.g., a high resistance material restrains flow of current from a power source (e.g., a battery of the vehicle, a dedicated battery for the heating element, etc.) that creates heat as a byproduct of the high resistance). The heat is conducted to the PM sensor 70. In other embodiments, the heating element 75 may include any type of heating element that is structured to burn off exhaust gas constituents from the PM sensor (e.g., a convective heating element that circulates hot exhaust gas substantially around the PM sensor to burn off the constituents). All such variations are intended to fall within the spirit and scope of the present disclosure. According to one embodiment, the heating element 75 is communicably coupled to the controller 100, such that controller 100 controls its operation. According to another embodiment, the heating element 75 is pre-programmed with a heating schedule (e.g., the stepped temperature heating schedule described below), such that activation of the heating schedule is based on the measurements (e.g., the measured resistance) of the PM sensor 70. All such variations are intended to fall within the spirit and scope of the present disclosure.

Referring back to FIG. 1, in one embodiment, the controller 100 is structured to control the operation of the engine system 10 and associated sub-systems, such as the internal combustion engine 20 and the exhaust gas aftertreatment system 22. According to one embodiment, the components of FIG. 1 are embodied in a vehicle. In various alternate embodiments, as described above, the controller 100 may be used with any engine-exhaust aftertreatment system. The vehicle may include an on-road or an off-road vehicle including, but not limited to, line-haul trucks, mid-range trucks (e.g., pick-up trucks), tanks, airplanes, and any other type of vehicle that utilizes an exhaust aftertreatment system. Communication between and among the components may be via any number of wired or wireless connections. For example, a wired connection may include a serial cable, a fiber optic cable, a CAT5 cable, or any other form of wired connection. In comparison, a wireless connection may include the Internet, Wi-Fi, cellular, radio, etc. In one embodiment, a controller area network (CAN) bus provides the exchange of signals, information, and/or data. The CAN bus includes any number of wired and wireless connections. Because the controller 100 is communicably coupled to the systems and components of FIG. 1, the controller 100 is structured to receive data from one or more of the components shown in FIG. 1. For example, the data may include particulate matter data, which provides an indication of a state of the PM sensor 70 (e.g., a full state may indicate that particulate matter has accumulated to above a threshold level). For example, the particulate matter data may include a measured resistance across the PM sensor 70 (For example, across the sensor 70 as a whole, between traces, etc. All such variations are intended to fall within the spirit and scope of the present disclosure). The data may also include a temperature of the heating element 75, such that the controller 100 may monitor an approximate temperature of heat being provided by the heating element 75 to the PM sensor 70.

Figure 3:
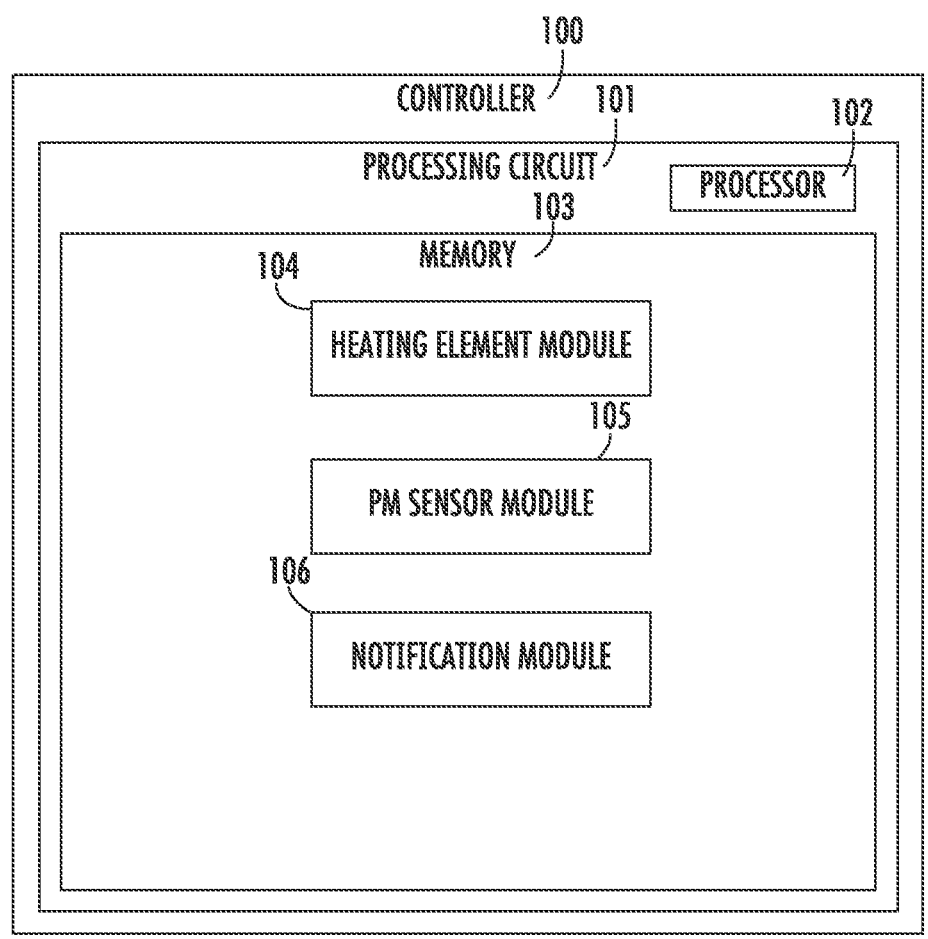
FIG. 3 is a schematic diagram of an exemplary controller used with the system of FIG. 1.

Referring now to FIG. 3, an example structure for the controller 100 is shown according to one embodiment. As shown, the controller 100 includes a processing circuit 101 including a processor 102 and a memory 103. The processor 102 may be implemented as a general-purpose processor, an application specific integrated circuit (ASIC), one or more field programmable gate arrays (FPGAs), a digital signal processor (DSP), a group of processing components, or other suitable electronic processing components. The one or more memory devices 103 (e.g., NVRAM, RAM, ROM, Flash Memory, hard disk storage, etc.) may store data and/or computer code for facilitating the various processes described herein. Thus, the one or more memory devices 103 may be communicably connected to the processor 102 and provide computer code or instructions to the processor 102 for executing the processes described in regard to the controller 100 herein. Moreover, the one or more memory devices 103 may be or include tangible, non-transient volatile memory or non-volatile memory. Accordingly, the one or more memory devices 103 may include database components, object code components, script components, or any other type of information structure for supporting the various activities and information structures described herein.

In certain embodiments, the controller 100 may be embodied in one or more apparatuses in a vehicle where the engine-exhaust aftertreatment system is embodied within (e.g., an engine control unit, an aftertreatment system control unit, etc.). In other embodiments, the controller 100 may be embodied in a diagnostic tool. In this configuration, a service technician may troubleshoot the PM sensor 70 via connection of the controller 100 with the PM sensor 70 and heating element 75. All such variations are intended to fall within the spirit and scope of the present disclosure.

The memory 103 is shown to include various modules for completing the activities described herein. More particularly, the memory 103 includes modules structured to control the heating element 75 of the PM sensor 70 to substantially prevent uncontrolled combustion of accumulated exhaust gas constituents on the PM sensor 70 in order to prolong life of the PM sensor 70 and restore its functionality. While various modules with particular functionality are shown in FIG. 3, it should be understood that the controller 100 and memory 103 may include any number of modules for completing the functions described herein. For example, the activities of multiple modules may be combined as a single module, additional modules with additional functionality, etc. Further, it should be understood that the controller 100 may further control other vehicle activity beyond the scope of the present disclosure.

As shown, the controller 100 includes a heating element module 104 communicably coupled to a particulate matter (PM) sensor module 105, and a notification module 106 communicably coupled to the heat element module 104 and the PM sensor module 105. The PM sensor module 105 is structured to receive particulate matter data from the PM sensor 70. Accordingly, in one embodiment, the PM sensor module 105 may include the PM sensor 70; in another embodiment, the PM sensor module 105 may include communication circuitry for facilitating the exchange of information between the PM sensor 70 and the PM sensor module 105; and, in yet another embodiment, the PM sensor module 105 may include machine-readable content for facilitating the exchange of information between the PM sensor module 105 and the PM sensor 70. In the latter embodiment, the machine-readable content may be stored by the memory 103 and executable by the processor 102 for facilitating the operations described herein in regard to the PM sensor module 105. In yet a further embodiment, the PM sensor module 105 may include any combination of communication circuitry, machine-readable content, and components such as the PM sensor 70.

According to one embodiment, the PM sensor 70 is structured as the interdigitated electrode PM sensor. Accordingly, the particulate matter data may include a measured resistance across the PM sensor 70. The frequency of measuring and providing the resistance data to the PM sensor module 105 may be predefined in the PM sensor module 105 based on the application. For example, in some embodiments, the resistance may be measured continuously and in other embodiments, the resistance may be measured based on at least one of a passage of a preset amount of time or a passage of a preset distance traveled by the vehicle.

According to one embodiment, the PM sensor 70 has a nominal resistance threshold. (e.g., 10 mega ohms between the inlet and outlet ends, 73 and 74, of the PM sensor 70; or 1 mega ohm between electrodes (digits); etc.). If the measured resistance is at or below the nominal resistance threshold, the PM sensor module 105 may determine that the PM sensor is in a full state. At which point, the heater module 105 may be notified to begin activation of the heating element 75. It should be understood that the nominal resistance threshold of the PM sensor may vary based on the type of PM sensor used and/or the application of the PM sensor (e.g., exhaust aftertreatment systems that include DOCs may utilize a relatively higher nominal resistance threshold because some particulate matter may be oxidized by the DOC, such that if the resistance falls at or below the relatively higher threshold, the controller may determine that at least one of the DOC and DPF are working incorrectly).

According to another embodiment, the PM sensor module 105 may determine that the PM sensor is in a full state when it is not or, conversely, that it is not in a full state when it is. This type of false determination is referred to as poisoned. One type of poisoning covers the surface in a non-conductive surface and will not indicate a full sensor state when the proper amount of soot has been deposited. The other type of poisoning experiences a change in the surface such that the gap 71 instead of being an insulator becomes a conductor (either only at certain temperatures or at all temperatures).

According to one embodiment, the PM sensor module 105 also receives temperature data that provides an indication of the temperature of the PM sensor 70. In this embodiment, the PM sensor 70 may include a dedicated temperature sensor to measure the temperature. In other embodiments, an indication of the temperature of the PM sensor 70 may be determined from a temperature sensor in relatively close proximity of the sensor 70, or the temperature may be sensed remotely (e.g., temperature sensor 18 of FIG. 1, or from infra-red intensity). The PM sensor 70 temperature data may be utilized by the heater module 104 to control operation of the heating element 75 (e.g., when activation of the second temperature range is commanded). For example, the temperature data may provide an indication of when a certain temperature has been met for the PM sensor and then hold that temperature for a certain duration before activation of a subsequent temperature for the PM sensor.

According to another embodiment, the PM sensor module 105 may be structured to receive exhaust gas constituent data. The exhaust gas constituent data may provide an indication of the type and amount of a particular exhaust gas constituent in the PM sensor 70. Because the controller 100 may selectively operate the heating element 75 in a stepped-up temperature fashion to control burn-off of the exhaust gas constituents in the gap 71 of the PM sensor 70, a tracking of the exhaust gas constituents may impact the temperature range of the heating element 75 commanded by the controller 100. To monitor the constituents accumulated by the PM sensor 70, an exhaust gas analyzer may be placed upstream of the PM sensor 70. The exhaust gas analyzer tracks the amount of each type of exhaust gas constituent (e.g., carbon) in the exhaust gas stream. When the controller 100 is embodied in a separate diagnostic tool, the exhaust gas analyzer may be structured as a separate tool as well. Based on the analysis of the exhaust gas, an estimated amount of exhaust gas constituents in the PM sensor 70 may be determined (e.g., via a lookup table, a formula, an algorithm, etc.). In still other embodiments, an estimate of the exhaust gas constituents accumulated by the PM sensor 70 may be based on measurements received from other sensors in the engine-exhaust aftertreatment system of FIG. 1. For example, based on engine out NOx amount, an engine speed, a temperature at a specific location in the system, the controller 100 may estimate the amount of various constituents in the exhaust gas and estimate an accumulation rate of each of those constituents with the PM sensor 70. For example an ammonia ($NH_3$) sensor (e.g., NH3 sensor 72 in FIG. 1) may be placed near the PM sensor and the values from that could indicate the need for a melamine burn off heat of about 400 degrees Celsius.

The heating element module 104 is structured to operate the heating element 75 based on a determined state of the PM sensor 70. Accordingly, in one embodiment, the heating element module 104 may include the heating element 75; in another embodiment, the heating element module 104 may include communication circuitry for facilitating the exchange of information between the heating element module 104 and the heating element 75 (e.g., an instruction to cause operation of the heating element 75); and, in yet another embodiment, the heating element module 104 may include machine-readable content for facilitating the exchange of information between the heating element module 104 and the heating element 75. In the latter embodiment, the machine-readable content may be stored by the memory 103 and executable by the processor 102 for facilitating the operations described herein in regard to the heating element module 104. In yet a further embodiment, the heating element module 104 may include any combination of communication circuitry, machine-readable content, and components such as the heating element 75. According to one embodiment, if the PM sensor module 105 determines that the PM sensor 70 is in a filled or full state, the heating element module 104 activates the heating element 75. As mentioned above, a filled or full state may be determined based on a resistance across the PM sensor 70 being less than or equal to a nominal resistance threshold.

According to one embodiment, the controller 100 provides commands (e.g., via the heating element module 104) to increase the temperature of the heating element 75 in a step-up manner, where each subsequently commanded temperature range is higher (i.e., warmer) than the previous range. The delineations of each step (e.g., first step of 200 degrees Celsius for 10 seconds, second step of 400 degrees Celsius for 20 seconds, etc.) may be based at least in part on the type and estimated amount of an exhaust gas constituent in the PM sensor 70, as described above. In this case, the heating element 75 is activated to the burn-off temperature of that constituent(s) for a time period configured to burn-off the amount of that constituent(s). In other embodiments, the delineations may be predefined, such that the temperature elevations are independent of the amount and type of each constituent in the exhaust gas stream. These variations are best described in regard to FIG. 4 below.

The notification module 106 is structured to provide a notification to an operator. Accordingly, in one embodiment, the notification module 106 is communicably coupled to the operator I/O device 120. In another embodiment, the notification module 106 includes the operator I/O device 120. The notification may include, but is not limited to, a result of the sensor reconditioning (e.g., the result of the method 400), a fault code, a detected fault in one or more engine-exhaust aftertreatment components, etc.

Figure 4:
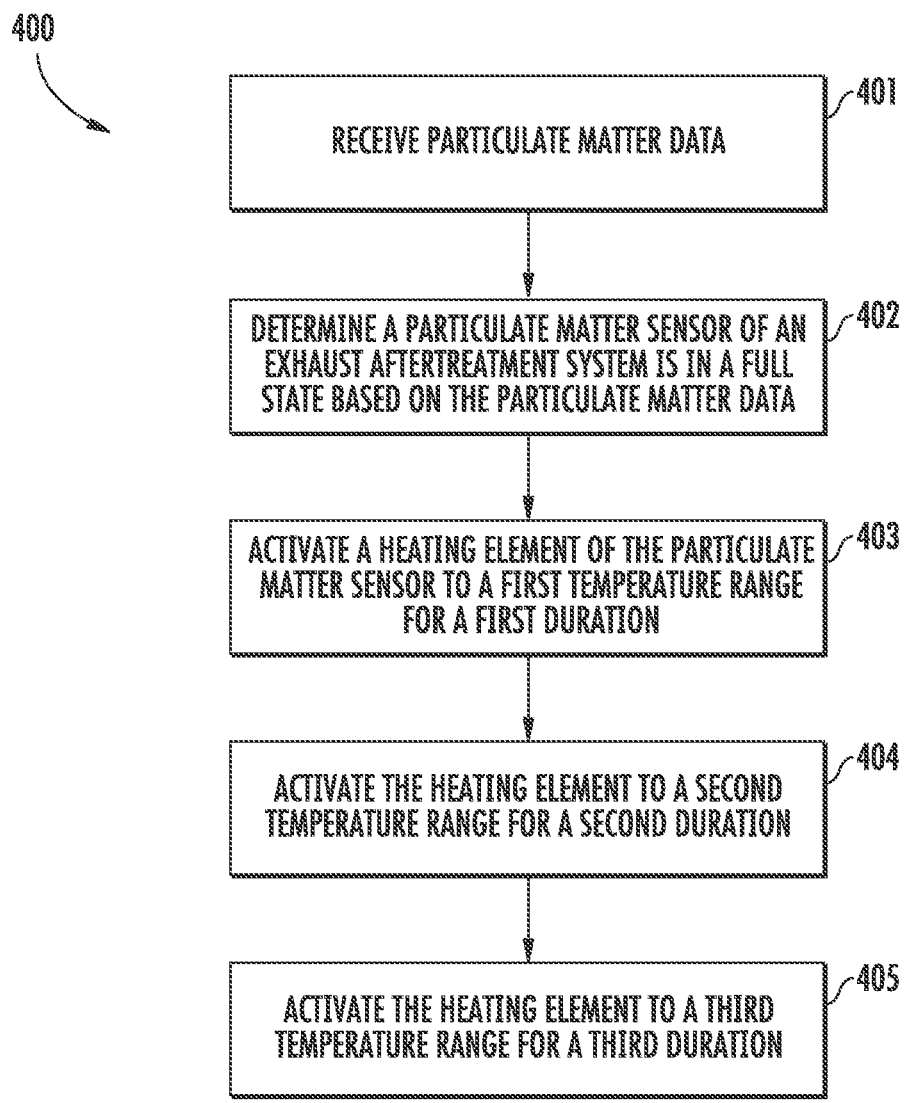
FIG. 4 is a flow diagram of a method of reconditioning a particulate matter sensor for an exhaust aftertreatment system, according to an example embodiment.
Figure 12:
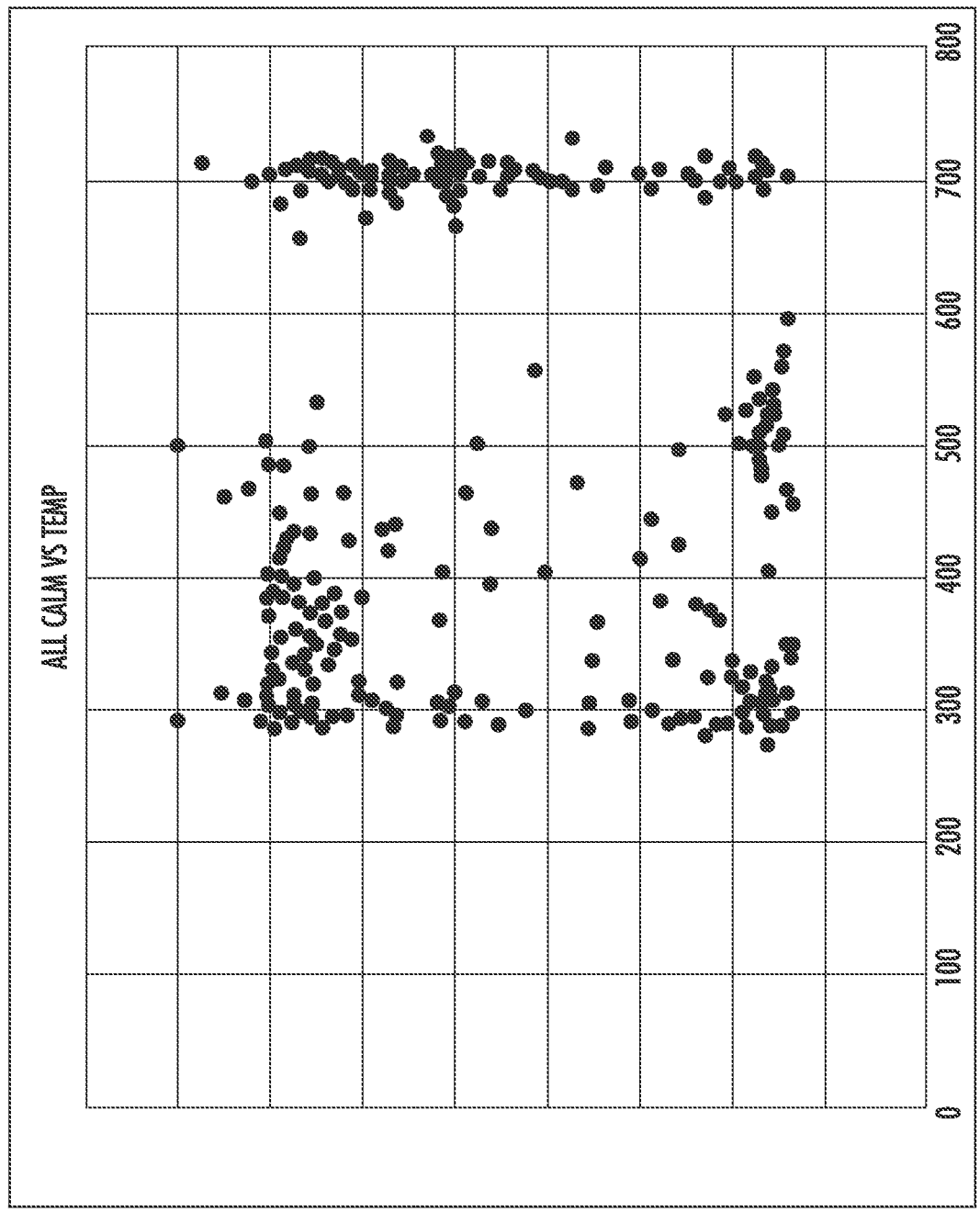
FIGS. 12-13 the depict graphical results of the table of FIGS. 11A-11F, according to an example embodiment.
Figure 13:
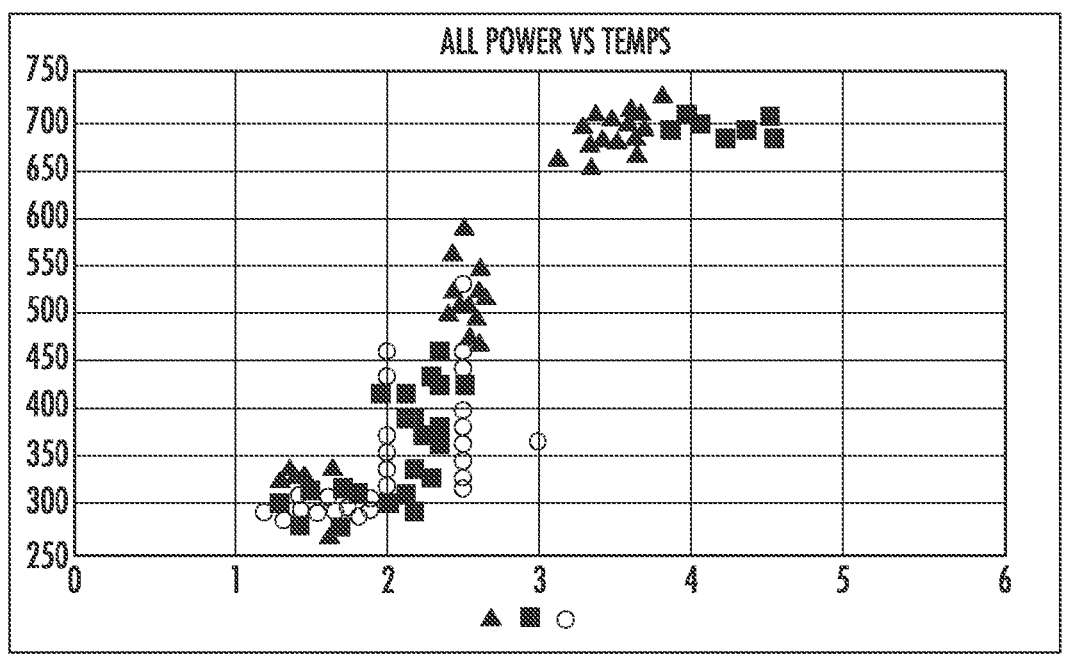

Referring to FIG. 4, a method 400 of reconditioning a particulate matter sensor for an exhaust aftertreatment system is shown according to an example embodiment. Because the method 400 may be implemented with the controller 100 described herein, various method 400 processes are described in regard to one or more of the modules below.

At process 401, particulate matter data is received. The particulate matter data provides an indication of a state of the particulate matter sensor. Accordingly, in one embodiment, the particulate matter data is a measured resistance across the interdigitated traces of a particulate matter sensor (e.g., PM sensor 70). In other embodiments, the particulate matter data may include any other type of data that indicates an amount of an exhaust gas accumulation in the particulate matter sensor (e.g., an estimate based on an exhaust gas flow) in order to provide an indication of a state of the particulate matter sensor. Based on the particulate matter data, a poisoned or full state for the particulate matter sensor is determined (process 402). In this example, the particulate matter sensor is structured as an interdigitated electrode particulate matter sensor. Accordingly, a filled or full state refers to the measured, estimated, and/or determined resistance across the sensor dropping to at or below a nominal resistance threshold for the sensor. In the alternative, a not full or filled state refers to the measured, estimated, and/or determined resistance across the PM sensor being above the nominal resistance threshold. As mentioned above, in one embodiment, a nominal resistance threshold for the sensor is approximately 10 mega ohms, where "approximately" refers to a predefined range with respect to the nominal value (e.g., +/−0.5 mega ohms) or any other definition used by those of ordinary skill in the art when defining resistance values.

In other embodiments, a poisoned state may be based on a duration of time between activations of the heating element for the particulate matter sensor (e.g., heating element 75). For example, if the resistance drops below the nominal resistance threshold (which triggers activation of the heating element) to cause activation of the heating element more than X times in a Y duration of time, then the controller 100 may determine that the particulate matter sensor is in a poisoned state. Although the particulate matter sensor is intended to monitor the health of the DPF, if the heating element is activated more than X times in Y duration of time, the controller 100 is structured to first troubleshoot the particulate matter sensor. As this poisoned condition is similar to the intended indication function of the PM sensor, great costs may be experienced such as a misdiagnosis of the DPF.

According to one embodiment, based on a filled state of the particulate matter sensor being determined, the heating element is activated a number of times at intermittent temperatures prior to a final temperature which is high enough to fully clear the sensor (e.g., substantially achieve an empty state for the PM sensor). In this case, an empty state or fully clear condition may be determined based on a resistance across the PM sensor being at or above the nominal resistance threshold. This resistance may be measured between one or more interdigitated traces and/or be the resistance across the PM sensor as a whole. All such variations are intended to fall within the spirit and scope of the present disclosure. In other embodiments, an empty state may be based on a time-element: the resistance does not drop to below the nominal resistance threshold more than X times in a Y amount of time.

Still referring to FIG. 4, in another embodiment, the intermittent temperature heating strategy may follow processes 403-405. In other words, based on a filled state of the particulate matter sensor being determined, a heating element of the particulate matter sensor is activated to a first temperature range for a first duration (process 403). Upon completion of the first duration, the heating element is activated to a second temperature range for a second duration (process 404). Upon completion of the second duration, the heating element is activated to a third temperature range for a third duration (process 405). At the end of process 405, the method 400 may be re-run to test the particulate matter sensor further and/or further recondition the particulate matter sensor. In one embodiment, the method 400 is re-run until the particulate matter sensor is determined to not be in a filled state and/or that the filled state has existed through a predefined number of iterations. If the particulate matter sensor is still determined to be in the filled state for a predefined number of iterations, a notification may be provided via notification module 106 to an operator (e.g., via I/O device 120). For example, a message may be provided that says that "the particulate matter sensor has been reconditioned but a full state still seems to exist, please check the DPF." In this case, the DPF may be faulty such that an excess amount of particulate matter passes through the system (or, the particulate matter sensor may be faulty where reconditioning has no effect on the performance of the sensor). In any event, the sequential heating strategy of the present disclosure functions to keep poisoning from happening with the PM sensor. That is, in some embodiments, the reactive exhaust gas constituents are kept away from the most reactive portion (e.g., the highest temperature burn-off period) of the heating strategy. As a result, a prolonged life for the PM sensor may be achieved.

According to one embodiment, the first temperature range is less than the second temperature range, which is less than the third temperature range. In one embodiment, the controller 100 includes predefined delineations for the first, second, and third temperature ranges as well as the first, second, and third durations. An example configuration is as follows: a first temperature range of approximately (e.g., plus-or-minus 20 degrees Celsius) of 200 Degrees Celsius for approximately 15 seconds (e.g., plus-or-minus 2 seconds); a second temperature range of approximately 400 degrees Celsius for approximately 15 seconds; and a third temperature range of approximately at or above 700 degrees Celsius for approximately 15 seconds. In this example, the approximate total of the reconditioning is 45 seconds. Furthermore, here, each time duration delineation includes the ramp-up time (e.g., the time to go from the first temperature of approximately 200 degrees Celsius to approximately the second temperature range of 400 degrees Celsius). Accordingly, other than the ramp-up time, the heating element is commanded to substantially hold at each of the temperature ranges for each temperature range demarcation. In other embodiments, the ramp-up time duration may be excluded from the duration time for each heating level. In one embodiment, the ramp rates are chosen to achieve a relatively high amount of control in burning off of specific contaminants (i.e., exhaust gas constituents).

According to another embodiment, the first temperature range and duration is based on a burn-off temperature for a first exhaust gas constituent (or constituent), the second temperature range and duration is based on a burn-off temperature for a second exhaust gas constituent (or constituents), and the third temperature range and duration is based on a burn-off temperature for a third exhaust gas constituent (or constituents). As a reminder, the burn-off temperature refers to a temperature that decomposes and/or otherwise dislodges that specific constituent from a component to permit it to be expelled from the system. In this configuration, a user may specifically designate each constituent for each delineation, such that the controller 100 automatically activates the heating element 75 to that constituent's corresponding burn-off temperature and duration. For example, the first constituent could be lower boiling hydrocarbons and humidity, the second constituent could be remaining organic compounds that would otherwise combust with carbon, and the third constituent could be carbon because carbon typically has the highest burn-off temperature relative to the other exhaust gas constituents. As a result, the higher burn-off temperature carbon constituents are controllably burned off with a relatively lower possibility of being burned off with other compounds. In turn, any uncontrollable combustion from the combustion of the carbon with other compounds is substantially reduced, such that a relatively lower chance of damage from uncontrolled combustion to the particulate matter sensor occurs.

An example of the step-up burn-off functionality of the heating element 75 with various exhaust gas constituents is as follows. Based on experimental data (see FIGS. 5-11), ammonia has a burn-off temperature of approximately −33 degrees Celsius, urea and biuret of about 250 degrees Celsius, and melamine about 370 degrees Celsius. The term "approximately" as used to define the burn-off temperature may refer to an absolute variation (e.g., +/−X degrees Celsius) and/or any other term accepted by those of ordinary skill in the art to define an acceptable variation from the defined burn-off temperature. These constituents represent exhaust gas constituents that react with carbon during combustion to create an increase (e.g., uncontrollability, temperature, duration, space-occupying) in combustion and reactivity that may cause damage to the particulate matter sensor. Accordingly, in one embodiment, the first temperature is approximately 200 degrees Celsius to burn off humidity and to lower the burn-off temperature hydrocarbons, the second temperature is approximately 400 degrees Celsius to burn-off the aforementioned constituents, such that a third temperature is at or above approximately 700 degrees Celsius to burn-off the carbon depositions not impacted by the presence of those other constituents. In turn, a controlled reconditioning of the particulate matter sensor occurs to prolong its life.

In another embodiment, the controller 100 may activate the heating element 75 based on particulate matter data, wherein the particulate matter data provides an indication of the amount and type of constituent causing the poisoned state of the particulate matter sensor. As mentioned above, the amount and type of constituent may be based on data from an exhaust gas analyzer, cyclic voltammetric scans using the interdigitated traces as electrodes, an estimation based on an exhaust gas flow rate and/or various operating parameters of the engine-aftertreatment system (e.g., frequency and amount of dosing, engine speed and torque, etc.), and the like. In this case, the heating element 75 is activated to first, second, and third temperature ranges and durations based on an actual, estimated, and/or predicted amount of the amount and type of exhaust gas constituent in the particulate matter sensor. For example, the controller 100 may estimate there to be about 60 percent carbon and 40 percent of the aforementioned constituents (e.g., biuret, urea, melamine, and ammonia) lodged in the particulate matter sensor that are likely causing the resistance across the particulate matter sensor to be indicative of a full state. Due to the relatively higher amount of carbon, the controller 100 provides a command to stay at the carbon burn-off temperature (the third temperature and duration) for a relatively greater amount of time compared to the first and second temperature durations. In this case, the controller 100 is reactive to an actual, estimated, and/or predicted amount and type of constituents in the exhaust gas that are causing a full state for the particulate matter sensor.

With the aforementioned in mind, an example of the method 400 with the components of FIGS. 1-4 is as follows in regard to a vehicle embodiment. After ten hours of operation of the vehicle, the controller 100 receives particulate matter data indicating that the resistance across the particulate matter sensor has dropped below 5 mega ohms (i.e., the nominal resistance threshold). The controller 100 provides a command to activate the heating element in a step-up temperature fashion, wherein each step-up temperature range is based on a different exhaust gas constituent or group of constituents. In this case, the first temperature range and duration is intended to burn-off relatively lower burn-off temperature constituents (e.g., humidity and relatively low burn-off temperature hydrocarbons). The second temperature range and duration is intended to burn-off constituents with an intermediate burn-off temperature (e.g., approximately 400 degrees Celsius). The final and third temperature range and duration is intended to burn-off carbon constituents. Of the exhaust gas constituents, carbon has the relatively highest burn-off temperature, such that it is burned off last. With this functionality, the particulate matter sensor is reconditioned in a controlled fashion to avoid a volatile combustion situation between a variety of constituents. By combusting constituents in this manner, there is less likely to be an interaction between poisons and the components of the particulate matter sensor 75 in order to prolong its life. After the reconditioning cycle, the resistance across the particulate matter sensor is acquired to determine if the sensor is still in a full state.

Referring now to FIGS. 5A-13, various experimental setups with corresponding results that show the effect of various types and amounts of exhaust gas constituents in an interdigitated electrode particulate matter sensor are shown according to various example embodiments. These sets of experiments simulate the effects of various potential poisons on a specific type of sensor poisoning, semi-conductive behavior. FIGS. 5A-5B depict the experimental setup: an "A" baking protocol, a "B" baking protocol, and a "C" baking protocol (graph 503). These tests simulate the temperature the heating element would be activated to and the baking environment (graph 504), along with an amount and type of exhaust gas exposed to the sensor (graph 501), sensor specimen itself (graph 505), and the equipment used (graph 502). FIGS. 6A-6D and 7A-7E are tables depicting the results of each baking protocol based on the amount and type of exhaust gas constituent (potential poison) included on the sensor active area. In FIGS. 6A-6D, the overall graph is broken down as follows: the top and left most portion is shown in FIG. 6A, the bottom and left most portion is shown in FIG. 6B, the top and right most portion is shown in FIG. 6C, and the bottom and right most portion is shown in FIG. 6D. In FIGS. 7A-7E, the overall graph is broken down as follows: the top and left most portion is shown in FIG. 7A, the bottom and left most portion is shown in FIG. 7B, the top and middle portion is shown in FIG. 7C, the bottom and middle portion is shown in FIG. 7D, and the right most portion is shown in FIG. 7E with the top part (graph 701) and the bottom part (graph 702). In FIG. 7E, the shaded cells (e.g., cross-hatched) in the last six columns indicate a reconditioned resistance (i.e., where the constituent has been burned off and the functionality of the particulate matter sensor restored)—i.e., a healthy state for the sensor. These relative resistance values are measured at 700 degrees Celsius in order to determine the semi-conductive properties. FIGS. 8A-10B depict the results of each baking protocol (FIGS. 8A-8B corresponds with the results of baking protocol "A"; FIGS. 9A-9C corresponds with the results of baking protocol "B" (the graph of FIGS. 9A-9C is broken down as follows: the top and left most portion is shown in FIG. 9A, the bottom and left most portion is shown in FIG. 9B, and the top and bottom right most portions are shown in FIG. 9C); and FIGS. 10A-10C corresponds with the results of baking protocol "C" (the graph of FIGS. 10A-10C is broken down as follows: the top and left most portion is shown in FIG. 10A, the bottom and left most portion is shown in FIG. 10B, and the top and bottom right most portions are shown in FIG. 10C)). Lastly, FIGS. 11A-11F show a tabulation of all the results combined (e.g., FIGS. 8A-10C on one table) with corresponding graphs (FIGS. 12-13) to show the differences between each baking protocol when conditions remain constant. In FIGS. 11A-11F, the overall graph is broken down as follows: the top and left most portion is shown in FIG. 11A, the bottom and left most portion is shown in FIG. 11B, the top and intermediate portion is shown in FIG. 11C, the bottom and intermediate portion is shown in FIG. 11D, the top and right most portion is shown in FIG. 11E, and the bottom and right most portion is shown in FIG. 11F. As shown in FIGS. 5A-13, the type and amount of exhaust gas constituent included with the PM sensor 70 affects the temperature needed or substantially needed to dislodge the constituents.

The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in machine-readable medium for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in machine-readable medium (or computer-readable medium), the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone computer-readable package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Accordingly, the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system, comprising:
    an engine;
    an exhaust aftertreatment system in exhaust gas receiving communication with the engine, wherein the exhaust aftertreatment system includes a particulate matter sensor that includes a heating element structured to selectively provide heat to the particulate matter sensor; and
    a controller communicably coupled to the engine and the exhaust aftertreatment system, wherein the controller is structured to:
        receive particulate matter data indicating a state of the particulate matter sensor;
        determine that the particulate matter sensor is in a full state based on the particulate matter data; and
        activate the heating element a number of times at intermittent temperatures prior to a final temperature;
        wherein the activating the heating element a number of times includes activating the heating element to approximately 200 degrees Celsius for approximately 15 seconds followed by activating the heating element to approximately 400 degrees Celsius for approximately 15 seconds followed by activating the heating element to approximately at or above 700 degrees Celsius for approximately 15 seconds.

2. The system of claim 1, wherein the final temperature fully clears the sensor.

3. The system of claim 2, wherein a determination of sensor being fully clear is based on a measured resistance across the sensor being at or above a nominal resistance threshold.

4. The system of claim 1, wherein the controller is structured to:
    activate the heating element of the particulate matter sensor to a first temperature range for a first duration;
    activate the heating element to a second temperature range for a second duration following the first duration; and
    activate the heating element to a third temperature range for a third duration following the second duration.

5. The system of claim 4, wherein the first temperature range and the first duration corresponds to a burn-off temperature and duration of a first constituent of an exhaust gas in the system, wherein the second temperature range and the second duration corresponds to a burn-off temperature and duration of a second constituent of the exhaust gas in the system, and wherein the third temperature range and the third duration corresponds to a burn-off temperature and duration of a third constituent of the exhaust gas in the system.

6. The system of claim 5, wherein the first constituent includes at least one of ammonia and water, wherein the second constituent includes at least one of urea, biuret, and melamine, and wherein the third constituent includes carbon.

7. The system of claim 4, wherein the first temperature range is less than the second temperature range, and wherein the second temperature range is less than the third temperature range.

8. The system of claim 1, wherein the full state is based on a resistance across the particulate matter sensor being less than a nominal resistance threshold.

9. The system of claim 1, wherein the particulate matter sensor is structured as an interdigitated electrode sensor.

10. A method for reconditioning a particulate matter sensor in an exhaust aftertreatment system, the method comprising:
    receiving particulate matter data indicating a state of a particulate matter sensor;
    determining that the particulate matter sensor is in a full state based on the particulate matter data;
    activating a heating element of the particulate matter sensor to a first temperature range for a first duration;
    activating the heating element to a second temperature range for a second duration following the first duration; and
    activating the heating element to a third temperature range for a third duration following the second duration,
    wherein the first temperature range is approximately 200 degrees Celsius and the first duration is approximately 15 seconds, wherein the second temperature range is approximately 400 degrees Celsius and the second duration is approximately 15 seconds, and wherein the third temperature range is approximately at or above 700 degrees Celsius and the third duration is approximately 15 seconds.

11. The method of claim 10, wherein the particulate matter sensor is structured as an interdigitated electrode sensor.

12. The method of claim 10, wherein the first temperature range and the first duration corresponds to a burn-off temperature and duration of a first constituent of an exhaust gas in the system, wherein the second temperature range and the second duration corresponds to a burn-off temperature and duration of a second constituent of the exhaust gas in the system, and wherein the third temperature range and the third duration corresponds to a burn-off temperature and duration of a third constituent of the exhaust gas in the system.

13. The method of claim 10, wherein the full state is based on a resistance across the particulate matter sensor being less than a nominal resistance threshold, wherein the nominal resistance threshold is approximately 10 mega ohms.

14. An apparatus, comprising:
    a particulate matter (PM) sensor module structured to receive particulate matter data and determine that a particulate matter sensor of an exhaust aftertreatment system is in a full state based on the particulate matter data; and a heating element module communicably coupled to the PM sensor module, wherein the heating element module is structured to activate a heating element of the particulate matter sensor a number of times at intermittent temperatures prior to a final temperature, the activating the heating element a number of times including activating the heating element to approximately 200 degrees Celsius for approximately 15 seconds followed by activating the heating element to approximately 400 degrees Celsius for approximately 15 seconds followed by activating the heating element to approximately at or above 700 degrees Celsius for approximately 15 seconds.

15. The apparatus of claim 14, wherein the heating element module is structured to:

activate the heating element of the particulate matter sensor to a first temperature range for a first duration;

activate the heating element to a second temperature range for a second duration following the first duration; and activate the heating element to a third temperature range for a third duration following the second duration.

16. The apparatus of claim 15, wherein the first temperature range and the first duration corresponds to a burn-off temperature and duration of a first constituent of an exhaust gas in the system, wherein the second temperature range and the second duration corresponds to a burn-off temperature and duration of a second constituent of the exhaust gas in the system, and wherein the third temperature range and the third duration corresponds to a burn-off temperature and duration of a third constituent of the exhaust gas in the system.

17. The apparatus of claim 16, wherein the first constituent includes at least one of ammonia and water, wherein the second constituent includes at least one of urea, biuret, and melamine, and wherein the third constituent includes carbon.

18. The apparatus of claim 15, wherein the first temperature range is less than the second temperature range, and wherein the second temperature range is less than the third temperature range.

* * * * *